(12) United States Patent
Emanuel et al.

(10) Patent No.: US 8,795,726 B2
(45) Date of Patent: Aug. 5, 2014

(54) SUSTAINED-RELEASE NUCLEIC ACID MATRIX COMPOSITIONS

(75) Inventors: Noam Emanuel, Rehovot (IL); Yosef Rosenfeld, Ness-Ziona (IL)

(73) Assignee: Polypid Ltd., Petach-Tikva (IL)

(*) Notice: Subject to any disclaimer, the term of this patent is extended or adjusted under 35 U.S.C. 154(b) by 0 days.

(21) Appl. No.: 13/574,040

(22) PCT Filed: Jan. 18, 2011

(86) PCT No.: PCT/IL2011/000054
§ 371 (c)(1),
(2), (4) Date: Jul. 19, 2012

(87) PCT Pub. No.: WO2011/089595
PCT Pub. Date: Jul. 28, 2011

(65) Prior Publication Data
US 2012/0294944 A1    Nov. 22, 2012

Related U.S. Application Data

(60) Provisional application No. 61/296,040, filed on Jan. 19, 2010.

(51) Int. Cl.
*A61K 9/26* (2006.01)

(52) U.S. Cl.
USPC .......... 424/469; 424/1.25; 424/1.29; 424/425

(58) Field of Classification Search
USPC ................................ 424/1.25, 1.29, 425, 469
See application file for complete search history.

(56) References Cited

U.S. PATENT DOCUMENTS

| | | |
|---|---|---|
| 3,773,919 A | 11/1973 | Boswell et al. |
| 4,522,803 A | 6/1985 | Lenk et al. |
| 4,578,384 A | 3/1986 | Hollinger |
| 4,882,167 A | 11/1989 | Jang |
| 5,043,166 A | 8/1991 | Barenholz et al. |
| 5,316,771 A | 5/1994 | Barenholz et al. |
| 5,837,221 A | 11/1998 | Bernstein et al. |
| 5,919,480 A | 7/1999 | Kedar et al. |
| 6,048,551 A | 4/2000 | Hilfinger et al. |
| 6,071,494 A | 6/2000 | Unger |
| 6,083,482 A | 7/2000 | Wang |
| 6,120,805 A | 9/2000 | Spenlehauer et al. |
| 6,156,337 A | 12/2000 | Barenholz et al. |
| 6,162,462 A | 12/2000 | Bolotin et al. |
| 6,238,702 B1 | 5/2001 | Berde et al. |
| 6,248,345 B1 | 6/2001 | Goldenheim et al. |
| 6,277,413 B1 | 8/2001 | Sankaram |
| 6,287,587 B2 | 9/2001 | Shigeyuki et al. |
| 6,333,021 B1 | 12/2001 | Schneider et al. |
| 6,403,057 B1 | 6/2002 | Schneider et al. |
| 6,787,132 B1 | 9/2004 | Gabizon et al. |
| 6,793,938 B2 * | 9/2004 | Sankaram ..................... 424/489 |
| 6,967,028 B2 | 11/2005 | Dulieu et al. |
| 7,045,146 B2 | 5/2006 | Caruso et al. |
| 7,160,554 B2 | 1/2007 | Zalipsky et al. |
| 2001/0000470 A1 | 4/2001 | Bernstein et al. |
| 2003/0113379 A1 | 6/2003 | Chen et al. |
| 2003/0161809 A1 | 8/2003 | Houston et al. |
| 2003/0228355 A1 | 12/2003 | Zarif et al. |
| 2004/0018327 A1 | 1/2004 | Wynn et al. |
| 2004/0115240 A1 | 6/2004 | Narhi et al. |
| 2004/0247624 A1 | 12/2004 | Unger et al. |
| 2005/0191344 A1 | 9/2005 | Zalipsky et al. |
| 2005/0208100 A1 | 9/2005 | Weber et al. |
| 2005/0249697 A1 | 11/2005 | Uhrich et al. |
| 2005/0287180 A1 | 12/2005 | Chen |
| 2006/0073203 A1 | 4/2006 | Ljusberg-Wahren et al. |
| 2006/0100370 A1 | 5/2006 | Wellisz et al. |
| 2006/0147520 A1 | 7/2006 | Ruegg |
| 2006/0188573 A1 | 8/2006 | Imberg |
| 2006/0189911 A1 | 8/2006 | Fukuhira et al. |
| 2007/0104565 A1* | 5/2007 | Badham et al. ............... 414/796 |
| 2007/0112438 A1 | 5/2007 | Fukuhira et al. |
| 2007/0141134 A1 | 6/2007 | Kosak |
| 2007/0280991 A1 | 12/2007 | Glauser et al. |
| 2008/0085263 A1 | 4/2008 | Thuresson et al. |
| 2008/0095849 A1 | 4/2008 | Wu et al. |
| 2008/0119494 A1 | 5/2008 | Young et al. |
| 2009/0171077 A1 | 7/2009 | Hong et al. |
| 2009/0259302 A1 | 10/2009 | Trollsas et al. |
| 2009/0318355 A1 | 12/2009 | Chen et al. |
| 2010/0196482 A1 | 8/2010 | Radovic-Moreno et al. |

FOREIGN PATENT DOCUMENTS

| | | |
|---|---|---|
| EP | 1098610 B1 | 4/2009 |
| EP | 2123274 A1 | 11/2009 |
| IL | 140899 | 5/2007 |
| JP | 61063613 A | 4/1986 |

(Continued)

OTHER PUBLICATIONS

Bildirici, Lale et al., (2000) Transfection of cells by immunoporation. Nature, vol. 405, p. 298.
Capecchi, Mario R. (1980) High efficiency transformation by direct microinjection of DNA into cultured mammalian cells. Cell, vol. 22, pp. 479-488.
Capito, Ramille M. et al., (2008) Self-assembly of large and small molecules into hierarchically ordered sacs and membranes. Science, vol. 319, pp. 1812-1816.
Evora, C. et al., (1998) Relating the phagocytosis of microparticles by alveolar macrophages to surface chemistry: the effect of 1,2-dipalmitoylphosphatidylcholine. Journal of Controlled Release, vol. 51, pp. 143-152.
Gao, X. et al., (1995) Cationic liposome-mediated gene transfer. Gene Ther, vol. 2, pp. 710-722.
Heyes, J. et al., (2005) Cationic lipid saturation influences intracellular delivery of encapsulated nucleic acids. J Control Release, vol. 107, pp. 276-287.

(Continued)

*Primary Examiner* — Ali Soroush
(74) *Attorney, Agent, or Firm* — Daniel Feigelson; Fourth Dimension IP

(57) ABSTRACT

The present invention provides compositions for extended release of a nucleic acid agent, a biodegradable polymer. The present invention also provides methods of producing the matrix compositions and methods for using the matrix compositions to provide controlled release of the nucleic acid agent.

22 Claims, 11 Drawing Sheets

(56) References Cited

FOREIGN PATENT DOCUMENTS

| | | | |
|---|---|---|---|
| JP | 4018035 | A | 1/1992 |
| JP | 4046115 | A | 2/1992 |
| WO | 91/07171 | A1 | 5/1991 |
| WO | 95/24929 | A2 | 9/1995 |
| WO | 96/21470 | A2 | 7/1996 |
| WO | 98/07412 | A1 | 2/1998 |
| WO | 99/55306 | A1 | 11/1999 |
| WO | 99/56731 | A1 | 11/1999 |
| WO | 00/03660 | A1 | 1/2000 |
| WO | 00/42989 | A2 | 7/2000 |
| WO | 00/78357 | A2 | 12/2000 |
| WO | 2008/105773 | A2 | 9/2008 |
| WO | 2008/124634 | A1 | 10/2008 |
| WO | 2009/006311 | A2 | 1/2009 |
| WO | 2009/058666 | A1 | 5/2009 |
| WO | 2009/061515 | A1 | 5/2009 |
| WO | 2009/110939 | A2 | 9/2009 |
| WO | 2009/127060 | A1 | 10/2009 |
| WO | 2010/007623 | A1 | 1/2010 |
| WO | 2010/078517 | A2 | 7/2010 |
| WO | 2010/135207 | A1 | 11/2010 |
| WO | 2011/007353 | A1 | 1/2011 |

OTHER PUBLICATIONS

Lu, James J. et al., (2009) A Novel Mechanism Is Involved in Cationic Lipid-Mediated Functional siRNA Delivery. Mol Pharm, vol. 6, No. 3, pp. 763-771.

Juni, Kazuhiko et al., (1985) Modification of the release rate of aclarubicin from polylactic acid microspheres by using additives. Chem Pharm Bull (Tokyo), vol. 33, No. 4, pp. 1734-1738.

Khoshnoodi, Jamshid et al., (2006) Molecular recognition in the assembly of collagens: terminal noncollagenous domains are key recognition modules in the formation of triple helical protomers. J Biol Chem, vol. 281, No. 50, pp. 38117-38121.

Martino, Sabata et al., (2009) Efficient siRNA Delivery by the Cationic Liposome DOTAP in Human Hematopoietic Stem Cells Differentiating into Dendritic Cells. Journal of Biomedicine and Biotechnology, vol. 2009, Article ID 410260, 7 pages.

Mosesson, M. W. (2005) Fibrinogen and fibrin structure and functions. J Thromb Haemost, vol. 3, pp. 1894-1904.

Thierry, Alain R. et al., (1995) Systemic gene therapy: biodistribution and long-term expression of a transgene in mice. Proc Natl Acad Sci USA, vol. 92, pp. 9742-9746.

Valenick, Leyla V. et al., (2005) Fibronectin fragmentation promotes $\alpha 4\beta 1$ integrin-mediated contraction of a fibrin-fibronectin provisional matrix. Exp Cell Res, vol. 309, pp. 48-55.

International Search Report and Written Opinion of PCT/IL09/00701 mailed Nov. 12, 2009, 9 pages.

International Search Report and Written Opinion of PCT/IL10/00563 mailed Oct. 29, 2010, 7 pages.

International Search Report of PCT/IL11/00054 mailed Aug. 25, 2011, 4 pages.

Requirement for Restriction/Election of U.S. Appl. No. 13/003,955 mailed Mar. 30, 2012, 9 pages.

Non-Final Office Action of U.S. Appl. No. 13/003,955 mailed May 24, 2012, 11 pages.

\* cited by examiner

DAY2

DAY5

DAY7

DAY9

DAY12

DAY14

SUSTAINED-RELEASE NUCLEIC ACID MATRIX COMPOSITIONS

CROSS REFERENCE TO RELATED APPLICATIONS

This application is a 35 U.S.C. §371 National Phase Entry Application from PCT/IL2011/000054, filed Jan. 18, 2011, and designating the United States, and claims priority to U.S. Patent Application No. 61/296,040 filed Jan. 19, 2010, which are incorporated herein in their entireties.

FIELD OF THE INVENTION

The present invention provides compositions for extended and/or controlled release of nucleic acid based drugs/agents, comprising a lipid-based matrix with a biocompatible polymer. The present invention also provides methods of producing the matrix compositions and methods for using the matrix compositions to provide controlled release of a nucleic acid active agent.

BACKGROUND OF THE INVENTION

Therapeutic Nucleic Acids

Gene therapy is a major area of research in drug development. Gene therapy has been considered a desirable mechanism to correct genetic defects resulting in diseases associated with failure to produce certain proteins and to overcome acquired diseases such as autoimmune diseases and cancer. Gene therapy could provide a new prophylactic approach for the treatment of many diseases. A technological barrier to commercialization of gene therapy, however, is the need for practical, effective and safe means for polynucleotide delivery and sustained and/or controlled release. Polynucleotides do not readily permeate the cellular membrane due to the charge repulsion between the negatively charged membrane and the high negative charge on the polynucleotide. As a result, polynucleotides have poor bioavailability and uptake into cells, typically <1%. In animal models, viral-based vectors have been used successfully to administer genes to a desired tissue. In some cases, these approaches have led to long-term (>2 years) expression of therapeutic levels of the protein. However, the limitations of viral-based approaches have been extensively reported. For instance, re-administration is not possible with these vectors because of the humoral immune response generated against the viral proteins. In addition to manufacturing challenges to obtain adequate reproducible vector supply, there are also significant safety concerns associated with viral vectors, particularly for those targeting the liver for gene expression. Not withstanding the problems associated with viral gene therapy, viruses have been considered by many to be more efficient than non-viral delivery vehicles.

The silencing or down regulation of specific gene expression in a cell can be affected by oligonucleic acids using techniques known as antisense therapy, RNA interference (RNAi), and enzymatic nucleic acid molecules. Antisense therapy refers to the process of inactivating target DNA or mRNA sequences through the use of complementary DNA or RNA oligonucleic acids, thereby inhibiting gene transcription or translation. An antisense molecule can be single stranded, double stranded or triple helix. Other agents capable of inhibiting expression are for example enzymatic nucleic acid molecules such as DNAzymes and ribozymes, capable of specifically cleaving an mRNA transcript of interest. DNAzymes are single-stranded deoxyribonucleotides that are capable of cleaving both single- and double-stranded target sequences. Ribozymes are catalytic ribonucleic acid molecules that are increasingly being used for the sequence-specific inhibition of gene expression by the cleavage of mRNAs encoding proteins of interest. RNA interference is a method of post-transcriptional inhibition of gene expression that is conserved throughout many eukaryotic organisms. It helps to control which genes are active and how active they are. Two types of small RNA molecules—microRNA (miRNA) and small interfering RNA (siRNA)—are central to RNA interference. RNAs are the direct products of genes, and these small RNAs can bind to specific other RNAs and either increase or decrease their activity, for example by preventing a messenger RNA from producing a protein. RNA interference has an important role in defending cells against parasitic genes—viruses and transposons—but also in directing development as well as gene expression in general. Although the RNA interference effect, which is mediated by small interfering RNA (siRNA) or micro-RNA, has potential application to human therapy, the hydrodynamic method usually used for rapid administration of oligonucleotides is unsuitable for use in humans. Development of RNAi-based therapeutics is relatively new to the pharmaceutical industry. Although many of the obstacles to the development of such drugs have been overcome, optimal delivery of the RNAi compounds to the appropriate tissues and into the cells is still a challenge.

Delivery of Nucleic Acids

A problem of non-viral gene therapy is to achieve the delivery and expression of sufficient nucleic acid to result in a tangible, physiologically relevant expression. Although DNA plasmids in isotonic saline (so-called "naked" DNA) were shown several years ago to transfect a variety of cells in vivo, such unprotected plasmids are susceptible to enzymatic degradation leading to irreproducibility in uptake and highly variable expression and biological responses in animal models. The very low bioavailability of "naked" plasmid in most tissues also requires high doses of plasmids to be administered to generate a pharmacological response. The field of non-viral gene delivery has therefore been directed to the development of more efficient synthetic delivery systems capable to increase the efficiency of plasmid delivery, confer prolonged expression and provide for storage stable formulations as is expected of other pharmaceutical formulations.

Chemical methods which facilitate the uptake of DNA by cells include the use of DEAE-Dextran. However this can result in loss of cell viability. Calcium phosphate is also a commonly used chemical agent which, when co-precipitated with DNA, introduces the DNA into cells.

Physical methods to introduce DNA have become effective means to reproducibly transfect cells. Direct microinjection is one such method which can deliver DNA directly to the nucleus of a cell (Capecchi 1980, Cell, 22, 479). This allows the analysis of single cell transfectants. So called "biolistic" methods physically insert DNA into cells and/or organelles using a high velocity particles coated with DNA. Electroporation is one of the most popular methods to transfect DNA. The method involves the use of a high voltage electrical charge to momentarily permeabilize cell membranes making them permeable to macromolecular complexes. However physical methods to introduce DNA do result in considerable loss of cell viability due to intracellular damage. More recently still a method termed immunoporation has become a recognized technique for the introduction of nucleic acid into cells, (Bildirici et al 2000, Nature, 405, 298). Transfection efficiency of between 40-50% is achievable depending on the nucleic acid used. These methods therefore require extensive optimization and also require expensive equipment.

To overcome the problem of degradation of nucleic acids, typically plasmid DNA ("pDNA"), or siRNAs/microRNA and enhance the efficiency of gene transfection, cationic condensing agents (such as polybrene, dendrimers, chitosan, lipids, and peptides) have been developed to protect the nucleic acids by condensing it through electrostatic interactions. However, the use of condensed plasmid particles for transfection of a large number of muscle cells in vivo, for example, has not been successful as compared to transfection of "naked" DNA.

Additional strategies that include the modulation of the plasmid surface charge and hydrophobicity by interaction with protective, interactive non-condensing systems have shown advantages over the use of "naked" DNA for direct administration to solid tissues (e.g., International Application Publication No. WO 96/21470).

Biodegradable microspheres that encapsulate the nucleic acid have also been used in gene delivery. For example, International Application Publication No. WO 00/78357 disclosed matrices, films, gels and hydrogels which include hyaluronic acid derivatized with a dihydrazide and crosslinked to a nucleic acid forming slow release microspheres.

Lipid based drug delivery systems are well known in the art of pharmaceutical science. Typically they are used to formulate drugs having poor bioavailability or high toxicity or both. Among the prevalent dosage forms that have gained acceptance are many different types of liposomes, including small unilamellar vesicles, multilamellar vesicles and many other types of liposomes; different types of emulsions, including water in oil emulsions, oil in water emulsions, water-in-oil-in-water double emulsions, submicron emulsions, microemulsions; micelles and many other hydrophobic drug carriers. These types of lipid based delivery systems can be highly specialized to permit targeted drug delivery or decreased toxicity or increased metabolic stability and the like. Extended release in the range of days, weeks and more are not profiles commonly associated with lipid based drug delivery systems in vivo. Liposomes that consist of amphiphilic cationic molecules are useful non-viral vectors for gene delivery in vitro and in vivo. In theory, the cationic head of the lipid associates with the negatively charged nucleic acid backbone of the DNA to form lipid:nucleic acid complexes. The lipid: nucleic acid complexes have several advantages as gene transfer vectors. Unlike viral vectors, the lipid:nucleic acid complexes can be used to transfer expression cassettes of essentially unlimited size. Since the complexes lack proteins, they may evoke fewer immunogenic and inflammatory responses. Moreover, they cannot replicate or recombine to form an infectious agent and have low integration frequency. The use of cationic lipids (e.g. liposomes) has become a common method since it does not have the degree of toxicity shown by chemical methods.

There are a number of publications that demonstrate convincingly that amphiphilic cationic lipids can mediate gene delivery in vivo and in vitro, by showing detectable expression of a reporter gene in culture cells in vitro. Because lipid:nucleic acid complexes are on occasion not as efficient as viral vectors for achieving successful gene transfer, much effort has been devoted in finding cationic lipids with increased transfection efficiency (Gao et al., 1995, Gene Therapy 2, 710-722).

Several works have reported the use of amphiphilic cationic lipid:nucleic acid complexes for in vivo transfection both in animals, and in humans (reviewed in Thierry et al., Proc. Natl. Acad. Sci. USA 1995, 92, 9742-9746). However, the technical problems for preparation of complexes having stable shelf-lives have not been addressed. For example, unlike viral vector preparations, lipid:nucleic acid complexes are unstable in terms of particle size. It is therefore difficult to obtain homogeneous lipid:nucleic acid complexes with a size distribution suitable for systemic injection. Most preparations of lipid:nucleic acid complexes are metastable. Consequently, these complexes typically must be used within a short period of time ranging from 30 minutes to a few hours. In clinical trials using cationic lipids as a carrier for DNA delivery, the two components were mixed at the bed-side and used immediately. The structural instability along with the loss of transfection activity of lipid:nucleic acid complex with time have been challenges for the future development of lipid-mediated gene therapy. Many of the recent developments in the field have focused on modification of the cationic system by combining a proven cationic delivery agent with another moiety. However, cationic backbone conjugates have not been successful in overcoming toxicity and none are approved for therapeutic use.

International Application Publication No. WO 95/24929 disclosed encapsulation or dispersion of genes in a biocompatible matrix, preferably biodegradable polymeric matrix, where the gene is able to diffuse out of the matrix over an extended period of time. Preferably the matrix is in the form of a microparticle such as a microsphere, microcapsule, a film, an implant, or a coating on a device such as a stent.

U.S. Pat. No. 6,048,551 disclosed a controlled release gene delivery system utilizing poly (lactide-co-glycolide) (PLGA), hydroxypropylmethyl cellulose phthalate, cellulose acetate phthalate, and the Ludragit R, L, and E series of polymers and copolymer microspheres to encapsulate the gene vector.

U.S. Application Publication No. 20070141134 discloses compositions that enhance the intracellular delivery of polynucleotides, wherein a polynucleotide can be incorporated into a PEG shielded micelle particle to facilitate the delivery of the polynucleotide across a cellular membrane. Incorporation of the polynucleotide into the shielded micelle particle is provided by covalent and non-covalent means. Other cell targeting agents may also be covalently coupled to the shielded micelle particle to enhance localization in the body.

International Patent Application Publication No. WO 2008/124634 discloses a method for encapsulating nucleic acids, particularly siRNAs, shRNAs, microRNAs, gene therapy plasmids, and other oligonucleotides in biodegradable polymer, whereby the nucleic acids are formulated into reverse micelles composed of non-toxic and/or naturally-occurring lipids prior to nanoparticle formation by nanoprecipitation.

International Application Publication No. WO 2009/127060 discloses a nucleic acid-lipid particle, comprising, in addition to the nucleic acid, a cationic lipid, a non-cationic lipid and a conjugated lipid that inhibits aggregation of the particles.

International Patent Application Publication No. WO 2010/007623 to some inventors of the present invention, published after the priority date of the present invention, discloses compositions for extended release of hydrophobic molecules such as steroids and antibiotics, comprising a lipid-based matrix comprising a biodegradable polymer.

Ideally sustained release drug delivery systems should exhibit kinetic and other characteristics readily controlled by the types and ratios of the specific excipients used.

There remain an unmet need for improved nucleic acid compositions and methods for controlled and extended delivery of therapeutic nucleic acid agents to appropriate tissues and into cells for gene therapy. Nowhere in the prior art it was suggested that matrix compositions comprising lipids and biocompatible polymer will possess improved properties for delivering nucleic acid based agents.

SUMMARY OF THE INVENTION

The present invention provides compositions for extended release of nucleic acid agents, particularly nucleic acid-based drugs, comprising a lipid-based matrix comprising a biocompatible polymer. The matrix composition is particularly suitable for local delivery or local application of a nucleic acid agent. The present invention also provides methods of producing the matrix compositions and methods for using the matrix compositions to provide controlled and/or sustained release of an active nucleic-acid ingredient.

The present invention is based in part on the unexpected discovery that negatively charged nucleic acids present in a water-based solution comprising polyethylene glycol (PEG) can be efficiently loaded into a lipid-based matrix comprising at least one biocompatible polymer, wherein the polymer can be biodegradable polymer, non-biodegradable polymer or a combination thereof. Furthermore, the nucleic acid can be released from the matrix in a controlled and/or extended manner.

The matrix compositions of the present invention is advantageous over hitherto known compositions and matrices for nucleic acid delivery in that it combines efficient local delivery of nucleic acid agent to cells or tissues with controlled and/or sustained release of the nucleic acid agent.

In one aspect, the present invention provides a matrix composition comprising: (a) a pharmaceutically acceptable biocompatible polymer in association with a first lipid component comprising at least one lipid having a polar group; (b) a second lipid component comprising at least one phospholipid having fatty acid moieties of at least 14 carbons; (c) at least one nucleic acid agent and (d) polyethylene glycol (PEG), wherein the matrix composition is adapted for providing sustained and/or controlled release of the nucleic acid.

Any nucleic acid molecule having a therapeutic or diagnostic utility may be used as part of the matrix compositions of the present invention. The nucleic acid agent may include DNA molecules, RNA molecules, single, double, triple or quadruple stranded. Non-limitative list of nucleic acid agent includes: plasmid DNA, linear DNA, (poly- and oligo-nucleotide), chromosomal DNA, messenger RNA (mRNA), antisense DNA/RNA, RNAi, siRNA, microRNA (miRNA), ribosomal RNA, locked nucleic acid analogue (LNA), oligonucleotide DNA (ODN) single and double stranded, immunostimulating sequences (ISS), and ribozymes.

The nucleic acid agent according to the present invention may include natural molecules, modified molecules or artificial molecules.

According to certain embodiments, the nucleic acid has non covalent interactions with PEG.

According to certain embodiments, the PEG is a linear PEG having a molecular weight in the range of 1,000-10,000. According to typical embodiments, the PEG molecular weight is in the range of 1,000-8,000, more typically below 8,000. Biodegradable PEG molecules, particularly PEG molecules comprising degradable spacers having higher molecular weights can be also used according to the teachings of the present invention.

PEG molecules having a molecular weight of 5,000 or less are currently approved for pharmaceutical use. Thus, according to certain typical embodiments, the active PEG molecules have a molecular weight of up to 5,000.

According to some embodiments the matrix composition comprises at least one cationic lipid. According to certain embodiments, the cationic lipid is selected from the group consisting of DC-Cholesterol, 1,2-dioleoyl-3-trimethylammonium-propane (DOTAP), Dimethyldioctadecylammonium (DDAB), 1,2-dilauroyl-sn-glycero-3-ethylphosphocholine (Ethyl PC), 1,2-di-O-octadecenyl-3-trimethylammonium propane (DOTMA), and others. Each possibility represents a separate embodiment of the present invention.

According to certain embodiments, the biocompatible polymer is selected from the group consisting of biodegradable polymer, non-biodegradable polymer and a combination thereof. According to certain embodiments the biodegradable polymer comprises polyester selected from the group consisting of PLA (polylactic acid), PGA (poly glycolic acid), PLGA (poly (lactic-co-glycolic acid)) and combinations thereof. According to other embodiments, the non-biodegradable polymer is selected from the group consisting of polyethylene glycol (PEG), PEG acrylate, PEG methacrylate, methylmethacrylate, ethylmethacrylate, butylmethacrylate, 2-ethylhexylmethacrylate, laurylmethacrylate, hydroxylethyl methacrylate, 2-methacryloyloxyethylphosphorylcholine (MPC), polystyrene, derivatized polystyrene, polylysine, poly N-ethyl-4-vinyl-pyridinium bromide, polymethylacrylate, silicone, polyoxymethylene, polyurethane, polyamides, polypropylene, polyvinyl chloride, polymethacrylic acid, and derivatives thereof alone or as co-polymeric mixtures thereof. Each possibility represents a separate embodiment of the present invention.

According to additional embodiments, the non-biodegradable polymer and the biodegradable polymer form a block co-polymer, for example, PLGA-PEG-PLGA and the like.

According to certain embodiments the lipid having a polar group is selected from the group consisting of a sterol, a tocopherol and a phosphatidylethanolamine. According to certain particular embodiments, the lipid having a polar group is sterol or a derivative thereof. According to typical embodiments, the sterol is cholesterol.

According to certain embodiments the first lipid component is mixed with the biocompatible polymer to form a non-covalent association.

According to certain particular embodiments, the first lipid component is sterol or a derivative thereof and the biocompatible polymer is biodegradable polyester. According to these embodiments, the biodegradable polyester is associated with the sterol via non-covalent bonds.

According to some embodiments the second lipid component comprises a phosphatidylcholine or a derivative thereof. According to other embodiments the second lipid component comprises a mixture of phosphatidylcholines or derivatives thereof. According to yet other embodiments the second lipid component comprises a mixture of a phosphatidylcholine and a phosphatidylethanolamine or derivatives thereof. According to additional embodiments, the second lipid component further comprises a sterol and derivatives thereof. According to typical embodiments, the sterol is cholesterol. According to yet further embodiments the second lipid component comprises a mixture of phospholipids of various types. According to certain typical embodiments, the second lipid component further comprises at least one of a sphingolipid, a tocopherol and a pegylated lipid.

According to additional embodiments, the weight ratio of the total lipids to the biocompatible polymer is between 1:1 and 9:1 inclusive.

According to certain embodiments, the matrix composition is homogeneous. In other embodiments, the matrix composition is in the form of a lipid-based matrix whose shape and boundaries are determined by the biodegradable polymer. In yet further embodiments, the matrix composition is in the form of an implant.

In certain particular embodiments, the present invention provides a matrix composition comprising: (a) biodegradable polyester; (b) a sterol; (c) a phosphatidylethanolamine having fatty acid moieties of at least 14 carbons; (d) a phosphatidylcholine having fatty acid moieties of at least 14 carbons; (e) a nucleic acid agent and (f) PEG.

In certain embodiments the matrix composition comprises at least 50% lipid by weight. In certain additional embodiments, the matrix composition further comprises a targeting moiety.

In certain embodiments, the matrix composition is capable of being degraded in vivo to vesicles into which some or all the mass of the released nucleic acid is integrated. In other embodiments, the matrix composition is capable of being degraded in vivo to form vesicles into which the active agent and the targeting moiety are integrated. Each possibility represents a separate embodiment of the present invention.

According to an additional aspect the present invention provides a pharmaceutical composition comprising the matrix composition of the present invention and a pharmaceutically acceptable excipient.

According to certain embodiments, the matrix composition of the present invention is in the form of an implant, following removal of the organic solvents and water. In another embodiment, the implant is homogeneous. Each possibility represents a separate embodiment of the present invention.

According to certain embodiments, the process of creating an implant from a composition of the present invention comprises the steps of (a) creating a matrix composition according to a method of the present invention in the form of a bulk material; and (b) transferring the bulk material into a mold or solid receptacle of a desired shaped.

According to another aspect the present invention provides a method for producing a matrix composition for delivery and sustained and/or controlled release of a nucleic acid agent comprising:

(a) mixing into a first volatile organic solvent (i) a biocompatible polymer and (ii) a first lipid component comprising at least one lipid having a polar group;

(b) mixing polyethylene glycol into a water-based solution of the nucleic acid agent;

(c) mixing the solution obtained in step (b) with a second volatile organic solvent and a second lipid component comprising at least one phospholipid having fatty acid moieties of at least 14 carbons;

(d) mixing the solutions obtained in steps (a) and (c) to form a homogeneous mixture; and (e) removing the volatile solvents and water, thereby producing a homogeneous polymer-phospholipids matrix comprising the nucleic acid agent.

According to certain embodiments, step (c) optionally further comprises (i) removing the solvents by evaporation, freeze drying or centrifugation to form a sediment; and (ii) suspending the resulted sediment in the second volatile organic solvent.

The selection of the specific solvents is made according to the specific nucleic acid and other substances used in the particular formulation and the intended use of the active nucleic acid, and according to embodiments of the present invention described herein. The particular lipids forming the matrix of the present invention are selected according to the desired release rate of the nucleic acids and according to embodiments of the present invention described herein.

The solvents are typically removed by evaporation conducted at controlled temperature determined according to the properties of the solution obtained. Residues of the organic solvents and water are further removed using vacuum.

According to the present invention the use of different types of volatile organic solutions enable the formation of homogeneous water-resistant, lipid based matrix compositions. According to various embodiments the first and second solvents can be the same or different. According to some embodiments one solvent can be non-polar and the other preferably water-miscible.

According to certain embodiments, the matrix composition is substantially free of water. The term "substantially free of water" refers to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the matrix. Each possibility represents a separate embodiment of the present invention.

In other embodiments, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

According to certain typical embodiments, the present invention provides a method of producing a matrix composition, the method comprising the steps of (a) mixing into a non-polar volatile organic solvent (i) a biodegradable polyester and (ii) a sterol;

(b) mixing polyethylene glycol having a molecular weight in the range of 1,000-8,000 into a water-based solution of the nucleic acid agent;

(c) mixing the solution obtained in step (b) with a water-miscible volatile organic solvent containing phosphatidylethanolamine and/or phosphatidylcholine and/or sterol; and (d) mixing the solutions obtained in steps (a) and (c) to form a homogeneous mixture;

(e) removing the organic solvents and water; and (f) further removing the remaining solvent by vacuum.

According to certain embodiments, the biodegradable polyester is selected from the group consisting of PLA, PGA and PLGA. In other embodiments, the biodegradable polyester is any other suitable biodegradable polyester or polyamine known in the art. In yet additional embodiments, the mixture containing the non-polar, organic solvent is homogenized prior to mixing it with the water-miscible volatile organic solvent mixture. In other embodiments, the mixture containing the water-miscible, organic solvent is homogenized prior to mixing it with the mixture containing the non-polar, organic solvent. In certain embodiments, the polymer in the mixture of step (a) is lipid saturated. In additional embodiments, the matrix composition is lipid saturated. Each possibility represents a separate embodiment of the present invention.

The matrix composition of the present invention can be used for coating fully or partially the surface of different substrates. According to certain embodiments, substrates to be coated include at least one material selected from the group consisting of carbon fibers, stainless steel, cobalt-chromium, titanium alloy, tantalum, ceramic and collagen or gelatin. In other embodiments substrates may include any medical devices and bone filler particles. Bone filler particles can be any one of allogeneic (i.e., from human sources), xenogeneic (i.e., from animal sources) and artificial bone particles. In other embodiments a treatment using the coated substrates and administration of the coated substrates will follow procedures known in the art for treatment and administration of similar uncoated substrates.

It is to be emphasized that the sustained release period using the compositions of the present invention can be programmed taking into account four major factors: (i) the weight ratio between the polymer and the lipid content, specifically the phospholipid having fatty acid moieties of at least 14 carbons, (ii) the biochemical and/or biophysical properties of the biopolymer and the lipids; (iii) the ratio between the different lipids used in a given composition and (iv) the incubation time of the nucleic acid agent with polyethylene glycol.

Specifically, the degradation rate of the polymer and the fluidity of the lipid should be considered. For example, a PLGA (85:15) polymer will degrade slower than a PLGA (50:50) polymer. A phosphatidylcholine (14:0) is more fluid (less rigid and less ordered) at body temperature than a phosphatidylcholine (18:0). Thus, for example, the release rate of a nucleic acid agent incorporated in a matrix composition comprising PLGA (85:15) and phosphatidylcholine (18:0) will be slower than that of a nucleic acid agent incorporated in a matrix composed of PLGA (50:50) and phosphatidylcholine (14:0). Another aspect that will determine the release rate is the physical characteristics of the nucleic acids. In addition, the release rate of a nucleic acid agent, particularly nucleic acid based drug can further be controlled by the addition of other lipids into the formulation of the second lipid component. This can includes fatty acids of different length such as lauric acid (C12:0), membrane active sterols (such as cholesterol) or other phospholipids such as phosphatidylethanolamine. The incubation time of the nucleic acid agent with polyethylene glycol affects the release rate of the nucleic acids from the matrix. Longer incubation time, at the range of several hours leads to higher release rate. According to various embodiments the active agent is released from the composition over a desired period ranging between several days to several months.

According to certain embodiments, at least 30% of the nucleic acid based agent is released from the matrix composition at zero-order kinetics. According to other embodiments, at least 50% of the nucleic acid based agent is released from the composition at zero-order kinetics.

These and other features and advantages of the present invention will become more readily understood and appreciated from the detailed description of the invention that follows.

BRIEF DESCRIPTION OF THE DRAWINGS

FIG. 3A demonstrates a typical lipid vesicles released into the medium following hydration. FIG. 3B shows a green fluorescence emission from the same vesicles indicating that these vesicles contained the florescent probe.

DETAILED DESCRIPTION OF THE INVENTION

Figure 1:
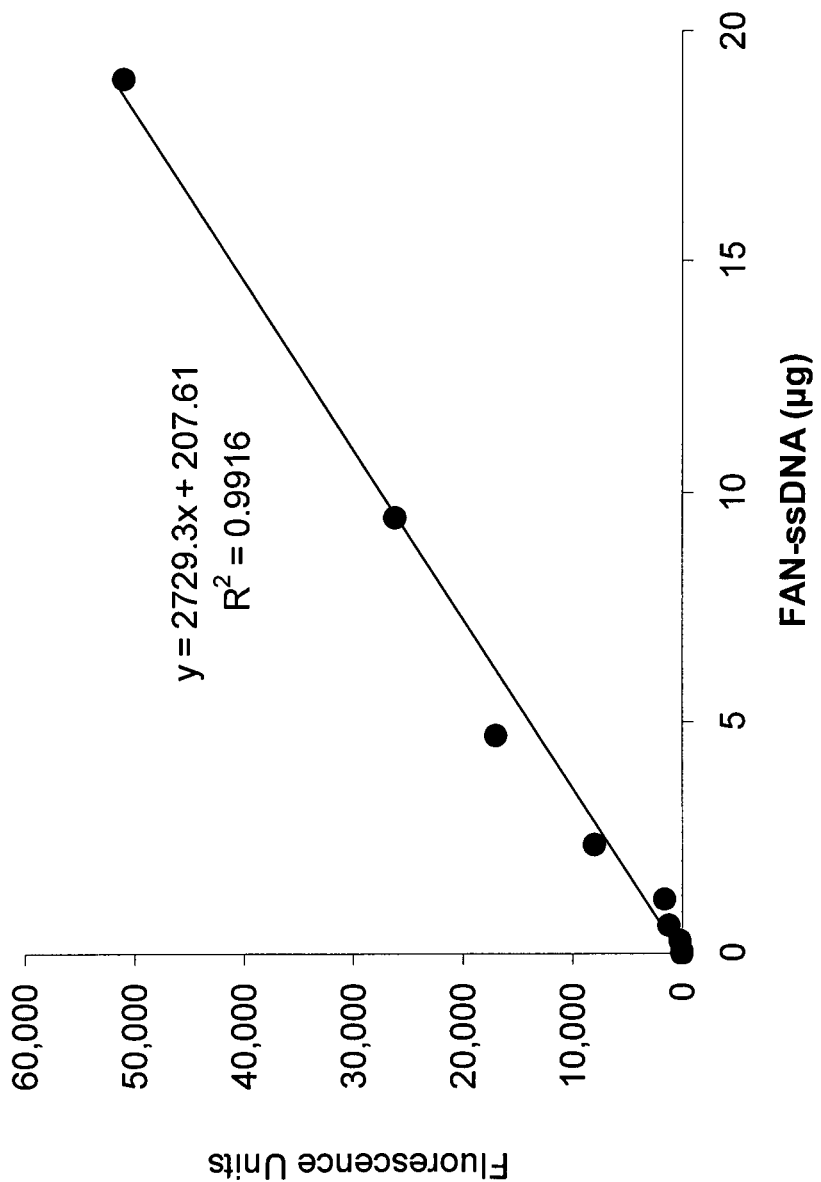
FIG. 1 is a standard curve showing the relation between ssDNA concentration and the fluorescence intensity of the fluorescent probe linked to the 5' end of the ssDNA FIG. 2 demonstrates the release rate over time (days) of ssDNA loaded into a matrix composition prepared without polyethylene glycol (PEG). The release rate was normalized to the estimated amount of ssDNA loaded.

The present invention provides compositions for extended and/or controlled release of nucleic-acids, comprising a lipid-based matrix with a biocompatible polymer. Particularly, the matrix compositions of the present invention are suitable for local release of the nucleic acids. The present invention also provides methods of producing the matrix compositions and methods for using the matrix compositions to provide controlled release of an active ingredient in the body of a subject in need thereof.

According to one aspect, the present invention provides a matrix composition comprising: (a) a pharmaceutically acceptable biocompatible polymer in association with a first lipid component comprising at least one lipid having a polar group; (b) a second lipid component comprising at least one phospholipid having fatty acid moieties of at least 14 carbons; (c) at least one nucleic acid agent; and (d) polyethylene glycol (PEG), wherein the matrix composition is adapted for providing sustained release of the nucleic acids.

According to certain embodiments, the biocompatible polymer is biodegradable. According to other embodiments, the biocompatible polymer is non-biodegradable. According to additional embodiments, the biocompatible polymer comprises a combination of biodegradable and non-biodegradable polymers, optionally as block co-polymer.

According to certain embodiments, the present invention provides a matrix composition comprising: (a) pharmaceutically acceptable biodegradable polyester; (b) a phospholipid having fatty acid moieties of at least 14 carbons: (c) a pharmaceutically active nucleic acid agent; and (d) PEG.

The nucleic acid agent comprises any nucleic acid molecule having a therapeutic or diagnostic utility. According to some embodiments the nucleic acid agent comprises a DNA molecule, an RNA molecule, single, double, triple or quadruple stranded. According to other embodiments the nucleic acid based agent is selected from the group consisting of: plasmid DNA, linear DNA, (poly- and oligo-nucleotide), chromosomal DNA, messenger RNA (mRNA), antisense DNA/RNA, RNAi, siRNA, microRNA (miRNA), ribosomal RNA, locked nucleic acid analogue (LNA), oligonucleotide DNA (ODN) single and double stranded, immunostimulating sequence (ISS), and ribozymes. According to certain typical embodiments, the nucleic acid agent is for therapeutic use.

According to some embodiments the lipid-saturated matrix composition comprises at least one cationic lipid. The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 3-(N—(N',N'-dimethylaminoethane)carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido)ethyl)N,N-dimethylammonium trifluoroacetate ("DOSPA") and ("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA). The following lipids are cationic and have a positive charge at below physiological pH: DODAP, DODMA, DMDMA and the like. Without wishing to be bound by any specific theory or mechanism of action, the cationic lipids of the matrix facilitate the internalization of the matrix of the invention, comprising nucleic acid agent, into cells or tissues. According to certain embodiments, the cells and/or tissues form part of the human body.

According to other embodiments the biodegradable polymer comprises cationic polymers, such as cationized guar gum, diallyl quaternary ammonium salt/acrylamide copolymers, quaternized polyvinylpyrrolidone and derivatives thereof, and various polyquaternium-compounds.

According to certain embodiments, the phospholipid of the second lipid component is a phosphatidylcholine having fatty acid moieties of at least 14 carbons. In another embodiment, the of the second lipid component further comprises a phosphatidylethanolamine having fatty acid moieties of at least 14 carbons. In another embodiment, the of the second lipid component further comprises sterol, particularly cholesterol.

In certain embodiments, the matrix composition is lipid saturated. "Lipid saturated," as used herein, refers to saturation of the polymer of the matrix composition with lipids including phospholipids, in combination with any nucleic acid agent and optionally a targeting moiety present in the matrix, and any other lipids that may be present. The matrix composition is saturated by whatever lipids are present. Lipid-saturated matrices of the present invention exhibit the additional advantage of not requiring a synthetic emulsifier or surfactant such as polyvinyl alcohol; thus, compositions of the present invention are typically substantially free of polyvinyl alcohol. Methods for determining the polymer:lipid ratio to attain lipid saturation and methods of determining the degree of lipid saturation of a matrix are known in the art.

In other embodiments, the matrix composition is homogeneous. In yet additional embodiments, the matrix composition is in the form of a lipid-saturated matrix whose shape and boundaries are determined by the biodegradable polymer. According to certain embodiments, the matrix composition is in the form of an implant.

In certain particular embodiments, the present invention provides a matrix composition comprising: (a) biodegradable polyester; (b) a sterol; (c) a phosphatidylethanolamine having fatty acid moieties of at least 14 carbons; (d) a phosphatidylcholine having fatty acid moieties of at least 14 carbons; (e) at least one nucleic acid based drug, and (f) PEG. In other typical embodiments, the matrix composition is lipid saturated.

In other typical embodiments, the present invention provides a matrix composition comprising: (a) biodegradable polyester; (b) a sterol; (c) a phosphatidylethanolamine having fatty acid moieties of at least 14 carbons; (d) a phosphatidylcholine having fatty acid moieties of at least 14 carbons; (e) a nucleic acid based active agent; and (f) PEG.

According to certain embodiments, the biodegradable polyester is associated with the sterol via non-covalent bonds.

As provided herein, the matrix of the present invention is capable of being molded into three-dimensional configurations of varying thickness and shape. Accordingly, the matrix formed can be produced to assume a specific shape including a sphere, cube, rod, tube, sheet, or into strings. In the case of employing freeze-drying steps during the preparation of the matrix, the shape is determined by the shape of a mold or support which may be made of any inert material and may be in contact with the matrix on all sides, as for a sphere or cube, or on a limited number of sides as for a sheet. The matrix may be shaped in the form of body cavities as required for implant design. Removing portions of the matrix with scissors, a scalpel, a laser beam or any other cutting instrument can create any refinements required in the three-dimensional structure. Each possibility represents a separate embodiment of the present invention.

According to additional embodiments, the matrix composition of the present invention provides a coating of bone graft material. According to certain embodiment, the bone graft material is selected from the group consisting of an allograft, an alloplast, and xenograft. According to further embodiments the matrix of the present invention can be combined with a collagen or collagen matrix protein.

Lipids

"Phosphatidylcholine" refers to a phosphoglyceride having a phosphorylcholine head group. Phosphatidylcholine compounds, in another embodiment, have the following structure:

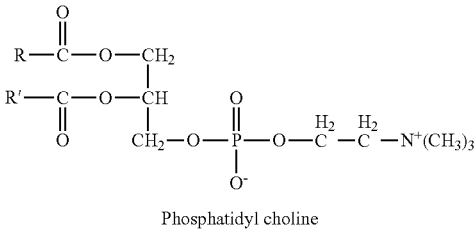

Phosphatidyl choline

The R and R' moieties are fatty acids, typically naturally occurring fatty acids or derivatives of naturally occurring fatty acids. In some embodiments, the fatty acid moieties are saturated fatty acid moieties. In some embodiments, the fatty acid moieties are unsaturated fatty acid moieties. "Saturated", refers to the absence of a double bond in the hydrocarbon chain. In another embodiment, the fatty acid moieties have at least 14 carbon atoms. In another embodiment, the fatty acid moieties have 16 carbon atoms. In another embodiment, the fatty acid moieties have 18 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are palmitoyl and stearoyl. In another embodiment, the fatty acid moieties are palmitoyl and arachidoyl. In another embodiment, the fatty acid moieties are arachidoyl and stearoyl. In another embodiment, the fatty acid moieties are both myristoyl. Each possibility represents a separate embodiment of the present invention.

In another embodiment, the phosphatidylcholine is a naturally-occurring phosphatidylcholine. In another embodiment, the phosphatidylcholine is a synthetic phosphatidylcholine. In another embodiment, the phosphatidylcholine contains a naturally-occurring distribution of isotopes. In another embodiment, the phosphatidylcholine is a deuterated phosphatidylcholine. Typically, the phosphatidylcholine is a symmetric phosphatidylcholine (i.e. a phosphatidylcholine wherein the two fatty acid moieties are identical). In another embodiment, the phosphatidylcholine is an asymmetric phosphatidylcholine.

Non-limiting examples of phosphatidylcholines are 1,2-distearoyl-sn-glycero-3-phosphocholine (DSPC), Dipalmitoyl-phosphatidylcholine (DPPC), Dimyristoyl-phosphatidylcholine (DMPC), dioleoyl-phosphatidylcholine (DOPC), 1-palmitoyl-2-oleoyl-phosphatidylcholine, and phosphatidylcholines modified with any of the fatty acid moieties enumerated hereinabove. In certain embodiments, the phosphatidylcholine is selected from the group consisting of DSPC, DPPC and DMPC. In another embodiment, the phosphatidylcholine is any other phosphatidylcholine known in the art. Each phosphatidylcholine represents a separate embodiment of the present invention.

Non-limiting examples of deuterated phosphatidylcholines are deuterated 1,2-distearoyl-sn-glycero-3-phosphocholine (deuterated DSPC), deuterated dioleoyl-phosphatidylcholine (deuterated DOPC), and deuterated 1-palmitoyl-2-oleoyl-phosphatidyl choline. In another embodiment, the phosphatidylcholine is selected from the group consisting of deuterated DSPC, deuterated DOPC, and deuterated 1-palmitoyl-2-oleoyl-phosphatidylcholine. In another embodiment, the phosphatidylcholine is any other deuterated phosphatidylcholine known in the art.

In certain embodiments, the phosphatidylcholine(s) (PC) compose at least 30% of the total lipid content of the matrix composition. In other embodiments, PC(s) compose at least 35% of the total lipid content, alternatively at least 40% of the total lipid content, yet alternatively at least 45%, at least 50%, least 55%, least 60%, at least 65%, at least 70%, at least 75%, at least 80%, at least 85%, at least 90% or at least 95% of the total lipid content. In another embodiment, PC(s) compose over 95% of the total lipid content. Each possibility represents a separate embodiment of the present invention.

"Phosphatidylethanolamine" refers to a phosphoglyceride having a phosphoryl ethanolamine head group. Phosphatidylethanolamine compounds, in another embodiment, have the following structure:

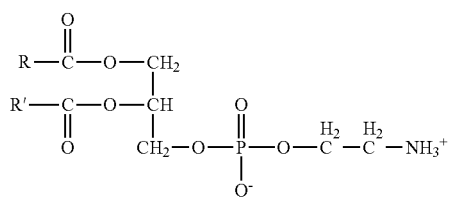

The R and R' moieties are fatty acids, typically naturally occurring fatty acids or derivatives of naturally occurring fatty acids. In another embodiment, the fatty acid moieties are saturated fatty acid moieties. "Saturated" in another embodiment, refers to the absence of a double bond in the hydrocarbon chain. In another embodiment, the fatty acid moieties have at least 14 carbon atoms. In another embodiment, the fatty acid moieties have at least 16 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are myristoyl and arachidoyl. In another embodiment, the fatty acid moieties are myristoyl and palmitoyl. In another embodiment, the fatty acid moieties are palmitoyl and stearoyl. In another embodiment, the fatty acid moieties are palmitoyl and arachidoyl. In another embodiment, the fatty acid moieties are arachidoyl and stearoyl. Each possibility represents a separate embodiment of the present invention.

In another embodiment, the phosphatidylethanolamine is a naturally-occurring phosphatidylethanolamine. In another embodiment, the phosphatidylethanolamine is a synthetic phosphatidylethanolamine. In another embodiment, the phosphatidylethanolamine is a deuterated phosphatidylethanolamine. In another embodiment, the phosphatidylethanolamine contains a naturally-occurring distribution of isotopes. Typically the phosphatidylethanolamine is a symmetric phosphatidylethanolamine. In another embodiment, the phosphatidylethanolamine is an asymmetric phosphatidylethanolamine.

Non-limiting examples of phosphatidylethanolamines are dimethyl dimyristoyl phosphatidylethanolamine (DMPE) and dipalmitoyl-phosphatidylethanolamine (DPPE), and phosphatidylethanolamines modified with any of the fatty acid moieties enumerated hereinabove. In another embodiment, the phosphatidylethanolamine is selected from the group consisting of DMPE and DPPE.

Non-limiting examples of deuterated phosphatidylethanolamines are deuterated DMPE and deuterated DPPE. In another embodiment, the phosphatidylethanolamine is selected from the group consisting of deuterated DMPE and deuterated DPPE. In another embodiment, the phosphatidylethanolamine is any other deuterated phosphatidylethanolamine known in the art.

In another embodiment, the phosphatidylethanolamine is any other phosphatidylethanolamine known in the art. Each phosphatidylethanolamine represents a separate embodiment of the present invention.

"Sterol" in one embodiment refers to a steroid with a hydroxyl group at the 3-position of the A-ring. In another embodiment, the term refers to a steroid having the

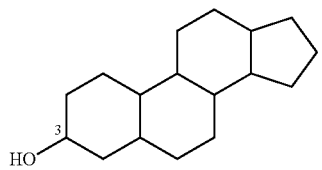 [SMILES: OC1CCC2C(CCC3C4CCCC4CCC23)C1]

In another embodiment, the sterol of methods and compositions of the present invention is a zoosterol. In another embodiment, the sterol is cholesterol:

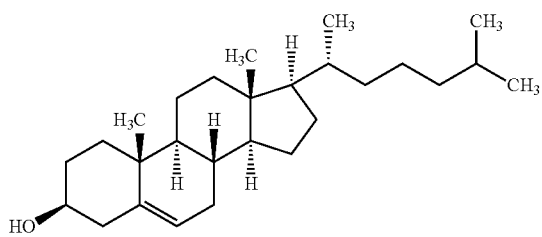

In another embodiment, the sterol is any other zoosterol known in the art. In another embodiment, the moles of sterol are up to 40% of the moles of total lipids present. In another embodiment, the sterol is incorporated into the matrix composition. Each possibility represents a separate embodiment of the present invention.

In another embodiment, the cholesterol is present in an amount of 10-60 percentage of the total weight of lipid content of the matrix composition. In another embodiment, the weight percentage is 20-50%. In another embodiment, the weight percentage is 10-40%. In another embodiment, the weight percentage is 30-50%. In another embodiment, the weight percentage is 20-60%. In another embodiment, the weight percentage is 25-55%. In another embodiment, the weight percentage is 35-55%. In another embodiment, the weight percentage is 30-60%. In another embodiment, the weight percentage is 30-55%. In another embodiment, the weight percentage is 20-50%. In another embodiment, the weight percentage is 25-55%. Each possibility represents a separate embodiment of the present invention.

In another embodiment, a composition of the present invention further comprises a lipid other than phosphatidylcholine, phosphatidylethanolamine, or a sterol. According to certain embodiments, the additional lipid is a phosphoglyceride. According to other embodiments, the additional lipid is selected from the group consisting of a phosphatidylserine, a phosphatidylglycerol, and a phosphatidylinositol. In yet additional embodiments, the additional lipid is selected from the group consisting of a phosphatidylserine, a phosphatidylglycerol, a phosphatidylinositol, and a sphingomyelin. According to yet further embodiments, a combination of any 2 or more of the above additional lipids is present within the matrix of the invention. According to certain embodiments, the polymer, phosphatidylcholine, phosphatidylethanolamine, sterol, and additional lipid(s) are all incorporated into the matrix composition. Each possibility represents a separate embodiment of the present invention.

According to yet additional embodiments, a composition of the present invention further comprises a phosphatidylserine. As used herein, "phosphatidylserine" refers to a phosphoglyceride having a phosphorylserine head group. Phosphatidylserine compounds, in another embodiment, have the following structure:

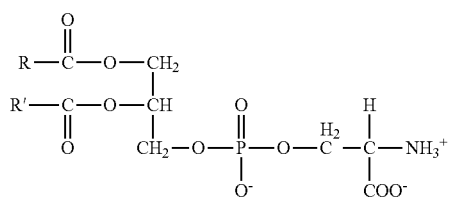

The R and R' moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

In other embodiments, the phosphatidylserine is a naturally-occurring phosphatidyl serine. In another embodiment, the phosphatidylserine is a synthetic phosphatidyl serine. In another embodiment, the phosphatidylserine is a deuterated phosphatidyl serine. In another embodiment, the phosphatidylserine contains a naturally-occurring distribution of isotopes. In another embodiment, the phosphatidylserine is a symmetric phosphatidylserine. In another embodiment, the phosphatidylserine is an asymmetric phosphatidylserine.

Non-limiting examples of phosphatidylserines are phosphatidylserines modified with any of the fatty acid moieties enumerated hereinabove. In another embodiment, the phosphatidylserine is any other phosphatidylserine known in the art. Each phosphatidylserine represents a separate embodiment of the present invention.

In other embodiments, a composition of the present invention further comprises a phosphatidylglycerol. "Phosphatidylglycerol" as used herein refers to a phosphoglyceride having a phosphoryl glycerol head group. Phosphatidylglycerol compounds, in another embodiment, have the following structure:

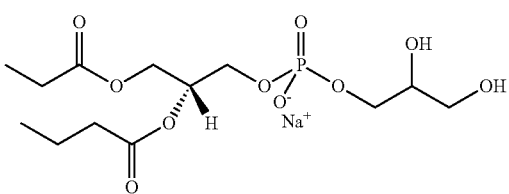 [SMILES: CCCC(=O)O[C@H](COC(=O)CC)COP(=O)([O-])OCC(O)CO ; [Na+]]

The 2 bonds to the left are connected to fatty acids, typically naturally occurring fatty acids or derivatives of naturally occurring fatty acids. In another embodiment, the phosphatidylglycerol is a naturally-occurring phosphatidylglycerol. In another embodiment, the phosphatidylglycerol is a synthetic phosphatidyl glycerol. In another embodiment, the phosphatidylglycerol is a deuterated phosphatidylglycerol. In another embodiment, the phosphatidylglycerol contains a naturally-occurring distribution of isotopes. In another embodiment, the phosphatidylglycerol is a symmetric phosphatidylglycerol. In another embodiment, the phosphatidylglycerol is an asymmetric phosphatidylglycerol. In another embodiment, the term includes diphosphatidylglycerol compounds having the following structure:

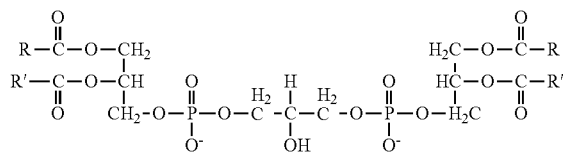

The R and R' moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

Non-limiting examples of phosphatidylglycerols are phosphatidylglycerols modified with any of the fatty acid moieties enumerated hereinabove. In another embodiment, the phosphatidylglycerol is any other phosphatidylglycerol known in the art. Each phosphatidylglycerol represents a separate embodiment of the present invention.

In yet additional embodiments, a composition of the present invention further comprises a phosphatidylinositol. As used herein, "phosphatidyl inositol" refers to a phosphoglyceride having a phosphorylinositol head group. Phosphatidylinositol compounds, in another embodiment, have the following structure:

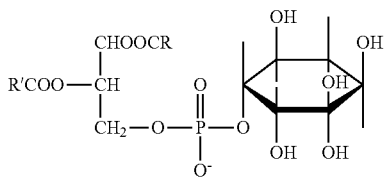

The R and R' moieties are fatty acids, typically naturally occurring fatty acids or derivatives of naturally occurring fatty acids. In another embodiment, the fatty acid moieties are saturated fatty acid moieties. In another embodiment, the fatty acid moieties have at least 14 carbon atoms. In another embodiment, the fatty acid moieties have at least 16 carbon atoms. In another embodiment, the fatty acid moieties are chosen such that the gel-to-liquid-crystal transition temperature of the resulting matrix is at least 40° C. In another embodiment, the fatty acid moieties are both myristoyl. In another embodiment, the fatty acid moieties are both palmitoyl. In another embodiment, the fatty acid moieties are both stearoyl. In another embodiment, the fatty acid moieties are both arachidoyl. In another embodiment, the fatty acid moieties are myristoyl and stearoyl. In another embodiment, the fatty acid moieties are a combination of two of the above fatty acid moieties.

In another embodiment, the phosphatidyl inositol is a naturally-occurring phosphatidylinositol. In another embodiment, the phosphatidylinositol is a synthetic phosphatidylinositol. In another embodiment, the phosphatidylinositol is a deuterated phosphatidylinositol. In another embodiment, the phosphatidylinositol contains a naturally-occurring distribution of isotopes. In another embodiment, the phosphatidylinositol is a symmetric phosphatidylinositol. In another embodiment, the phosphatidylinositol is an asymmetric phosphatidylinositol.

Non-limiting examples of phosphatidylinositols are phosphatidylinositols modified with any of the fatty acid moieties enumerated hereinabove. In another embodiment, the phosphatidylinositol is any other phosphatidylinositol known in the art. Each phosphatidylinositol represents a separate embodiment of the present invention.

In further embodiments, a composition of the present invention further comprises a sphingolipid. In certain embodiments, the sphingolipid is ceramide. In yet other embodiments, the sphingolipid is a sphingomyelin. "Sphingomyelin" refers to a sphingosine-derived phospholipid. Sphingomyelin compounds, in another embodiment, have the following structure:

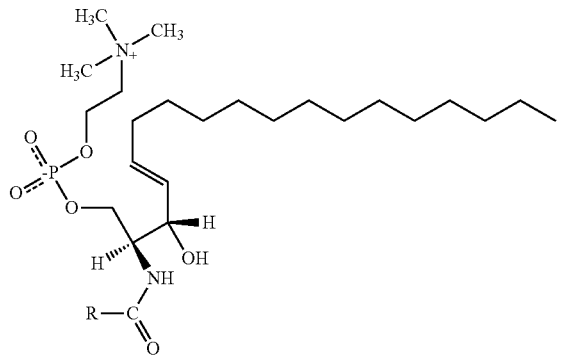

The R moiety is a fatty acid, typically a naturally occurring fatty acid or a derivative of a naturally occurring fatty acid. In another embodiment, the sphingomyelin is a naturally-occurring sphingomyelin. In another embodiment, the sphingomyelin is a synthetic sphingomyelin. In another embodiment, the sphingomyelin is a deuterated sphingomyelin. In another embodiment, the sphingomyelin contains a naturally-occurring distribution of isotopes.

In another embodiment, the fatty acid moiety of a sphingomyelin of methods and compositions of the present invention has at least 14 carbon atoms. In another embodiment, the fatty acid moiety has at least 16 carbon atoms. In another embodiment, the fatty acid moiety is chosen such that the gel-to-liquid-crystal transition temperature of the resulting matrix is at least 40° C.

Non-limiting examples of sphingomyelins are sphingomyelins modified with any of the fatty acid moieties enumerated hereinabove. In another embodiment, the sphingomyelin is any other sphingomyelin known in the art. Each sphingomyelin represents a separate embodiment of the present invention.

"Ceramide" refers to a compound having the structure:

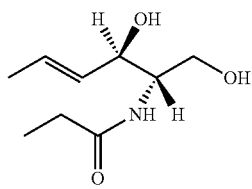

The 2 bonds to the left are connected to fatty acids, typically naturally occurring fatty acids or derivatives of naturally occurring fatty acids. In another embodiment, the fatty acids are longer-chain (to $C_{24}$ or greater). In another embodiment, the fatty acids are saturated fatty acids. In another embodiment, the fatty acids are monoenoic fatty acids. In another embodiment, the fatty acids are n-9 monoenoic fatty acids. In another embodiment, the fatty acids contain a hydroxyl group in position 2. In another embodiment, the fatty acids are other suitable fatty acids known in the art. In another embodiment, the ceramide is a naturally-occurring ceramide. In another embodiment, the ceramide is a synthetic ceramide. In another embodiment, the ceramide is incorporated into the matrix composition. Each possibility represents a separate embodiment of the present invention.

Each sphingolipid represents a separate embodiment of the present invention.

In certain embodiments, a composition of the present invention further comprises a pegylated lipid. In another embodiment, the PEG moiety has a MW of 500-5000 daltons. In another embodiment, the PEG moiety has any other suitable MW. Non-limiting examples of suitable PEG-modified lipids include PEG moieties with a methoxy end group, e.g. PEG-modified phosphatidylethanolamine and phosphatidic acid (structures A and B), PEG-modified diacylglycerols and dialkylglycerols (structures C and D), PEG-modified dialkylamines (structure E) and PEG-modified 1,2-diacyloxypropan-3-amines (structure F) as depicted below. In another embodiment, the PEG moiety has any other end group used in the art. In another embodiment, the pegylated lipid is selected from the group consisting of a PEG-modified phosphatidylethanolamine, a PEG-modified phosphatidic acid, a PEG-modified diacylglycerol, a PEG-modified dialkylglycerol, a PEG-modified dialkylamine, and a PEG-modified 1,2-diacyloxypropan-3-amine. In another embodiment, the pegylated lipid is any other pegylated phospholipid known in the art. Each possibility represents a separate embodiment of the present invention.

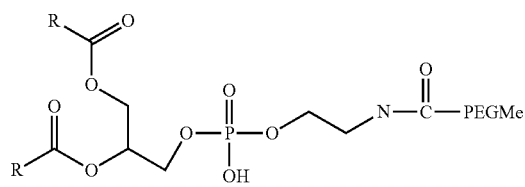

A

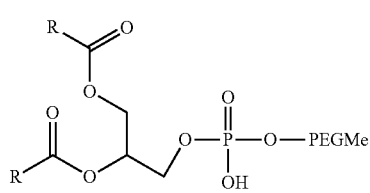

B

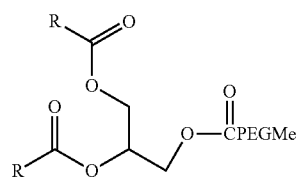

C

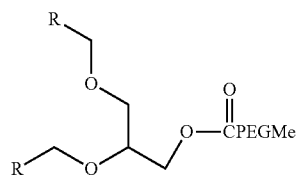

D

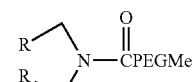

E

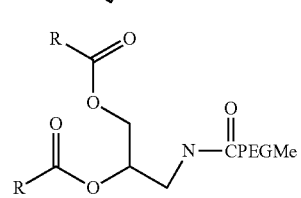

F

According to certain embodiments, the pegylated lipid is present in an amount of about 50 mole percent of total lipids in the matrix composition. In other embodiments, the percentage is about 45 mole %, alternatively about 40 mole %, about 35 mole about 30 mole %, about 25 mole %, about 20 mole %, about 15 mole %, about 10 mole %, and about 5 mole % or less. Each possibility represents a separate embodiment of the present invention.

Polymers

According to certain embodiments, the biocompatible polymer is biodegradable. According to certain currently typical embodiments, the biodegradable polymer is polyester.

According to certain embodiments, the biodegradable polyester employed according to the teachings of the present invention is PLA (polylactic acid). According to typical embodiments, "PLA" refers to poly(L-lactide), poly(D-lactide), and poly(DL-lactide). A representative structure of poly (DL-lactide) is depicted below:

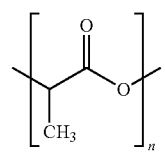

In other embodiments, the polymer is PGA (polyglycolic acid). In yet additional embodiments, the polymer is PLGA (poly(lactic-co-glycolic acid). The PLA contained in the PLGA may be any PLA known in the art, e.g. either enantiomer or a racemic mixture. A representative structure of PLGA is depicted below:

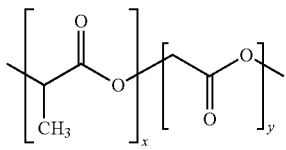

According to certain embodiments, the PLGA comprises a 1:1 lactic acid/glycolic acid ratio. In another embodiment, the ratio is 60:40. In another embodiment, the ratio is 70:30. In another embodiment, the ratio is 80:20. In another embodiment, the ratio is 90:10. In another embodiment, the ratio is 95:5. In another embodiment, the ratio is another ratio appropriate for an extended in vivo release profile, as defined herein. In another embodiment, the ratio is 50:50. In certain typical embodiments, the ratio is 75:25. The PLGA may be either a random or block copolymer. The PLGA may be also a block copolymer with other polymers such as PEG. Each possibility represents a separate embodiment of the present invention.

In another embodiment, the biodegradable polyester is selected from the group consisting of a polycaprolactone, a polyhydroxyalkanoate, a polypropylenefumarate, a polyorthoester, a polyanhydride, and a polyalkylcyanoacrylate, provided that the polyester contains a hydrogen bond acceptor moiety. In another embodiment, the biodegradable polyester is a block copolymer containing a combination of any two monomers selected from the group consisting of a PLA, PGA, a PLGA, polycaprolactone, a polyhydroxyalkanoate, a polypropylenefumarate, a polyorthoester, a polyanhydride, and a polyalkylcyanoacrylate. In another embodiment, the biodegradable polyester is a random copolymer containing a combination of any two of the monomers listed above. Each possibility represents a separate embodiment of the present invention.

The molecular weight (MW) of a biodegradable polyester according to the teachings of the present invention is, in another embodiment, between about 10-150 KDa. In another embodiment, the MW is between about 20-150 KDa. In another embodiment, the MW is between about 10-140 KDa. In another embodiment, the MW is between about 20-130 KDa. In another embodiment, the MW is between about 30-120 KDa. In another embodiment, the MW is between about 45-120 KDa. In another typical embodiment, the MW is between about 60-110 KDa. In another embodiment, a mixture of PLGA polymers of different MW is utilized. In another embodiment, the different polymers both have a MW in one of the above ranges. Each possibility represents a separate embodiment of the present invention.

In another embodiment, the biodegradable polymer is selected from the group of polyamines consisting of peptides containing one or more types of amino acids, with at least 10 amino acids.

"Biodegradable," as used herein, refers to a substance capable of being decomposed by natural biological processes at physiological pH. "Physiological pH" refers to the pH of body tissue, typically between 6-8. "Physiological pH" does not refer to the highly acidic pH of gastric juices, which is typically between 1 and 3.

According to some embodiments, the biocompatible polymer is non-biodegradable polymer. According to certain embodiments, the non-biodegradable polymer may be selected from the group consisting of, yet not limited to, polyethylene glycol, polyethylene glycol (PEG) acrylate, polymethacrylates (e.g. PEG methacrylate, polymethylmethacrylate, polyethylmethacrylate, polybutylmethacrylate, poly-2-ethylhexylmethacrylate, polylaurylmethacrylate, polyhydroxylethyl methacrylate), poly -methylacrylate, 2-methacryloyloxyethylphosphorylcholine (MPC), polystyrene, derivatized polystyrene, polylysine, poly N-ethyl-4-vinyl-pyridinium bromide, silicone, ethylene-vinyl acetate copolymers, polyethylenes, polypropylenes, polytetrafluoroethylenes, polyurethanes, polyacrylates, polyvinyl acetate, ethylene vinyl acetate, polyethylene, polyvinyl chloride, polyvinyl fluoride, copolymers of polymers of ethylene-vinyl acetates and acyl substituted cellulose acetates, poly(vinyl imidazole), chlorosulphonate polyolefins, polyethylene oxide, and mixtures thereof.

Nucleic Acid Agents

The nucleic acid agents or oligonucleotides of the present invention are preferably no more than about 1000 bases in length, typically no more than about 100 bases in length. In other typical embodiments, the oligonucleotides are no more than 30 nucleotides (or base pairs) in length. The nucleic acid agents may be single stranded, double stranded, triple helix, or any combination thereof. In case the nucleic acid agents include more than one strand, the strands do not necessarily need to be 100% complementary.

The terms "oligonucleotide", "oligonucleic acid" and "polynucleotide" are used interchangeably and refer to an oligomer or polymer of ribonucleic acids (ribo-oligonucleotide or ribo-oligonucleoside) or deoxyribonucleic acids. These terms include nucleic acid strands composed of naturally occurring nucleobases, sugars and covalent inter-sugar linkages as well as oligonucleotides having non-naturally occurring portions which function similarly. Such modified or substituted oligonucleotides may be preferred over native forms because of the valuable characteristics including, for example, increased stability in the presence of plasma nucleases and enhanced cellular uptake.

According to certain embodiments, the nucleic acids used according to the teachings of the present invention are antisense molecules. The term "antisense molecule", "antisense fragment" or "antisense" as used herein may refer to any polynucleotide having inhibitory antisense activity, said activity causing a decrease in the expression of the endogenous genomic copy of the corresponding gene. An antisense molecule is a polynucleotide which comprises consecutive nucleotides having a sequence of sufficient length and homology to a sequence present within the sequence of the target gene to permit hybridization of the antisense molecule to the gene. An antisense molecule may inactivate target DNA and/or RNA (such as, for example, mRNA, microRNA, and the like) sequences, and it may be single stranded, double stranded or triple helix. In case the antisense molecule includes more than one strand, the strands do not necessarily need to be 100% complementary.

RNA Interference (RNAi)

The term "RNA interference" or "RNAi" refers generally to a process in which a double-stranded RNA molecule changes the expression of a nucleic acid sequence with which the double-stranded or short hairpin RNA molecule shares substantial or total homology. The term "RNAi agent" refers to an RNA sequence that elicits RNAi.

Two types of small RNA molecules—microRNA (miRNA) and small interfering RNA (siRNA)—are central to RNA interference. RNAs are the direct products of genes, and these small RNAs can bind to specific other RNAs and either increase or decrease their activity, for example by preventing a messenger RNA from producing a protein. RNA interference has an important role in the natural defense of cells against parasitic genes—viruses and transposons—but also in directing development as well as gene expression in general.

The term "microRNA" or "miRNA" is used herein in accordance with its ordinary meaning in the art. miRNAs are single-stranded non coding RNA molecules of about 18-26 nucleotides. miRNAs are processed from primary transcripts known as pri-miRNA to short stem-loop structures called pre-miRNA and finally to functional miRNA. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). Mature miRNA molecules are partially complementary to one or more messenger RNA (mRNA) molecules, and they function to regulate gene expression. Examples of miRNAs to be used according to embodiments of the present invention include and yet are not limited to miRNA found in the miRNA database known as miRBase (http://microrna.sanger.ac.uk/).

"Small interfering RNA", also referred to as "short interfering RNA" or "siRNA", are short double stranded RNA ("dsRNA") molecules, which are present in the cell. dsRNA cause the destruction of messenger RNAs ("mRNAs") that share sequence homology with the siRNA to within one nucleotide resolution. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Typically, an siRNA is a double-stranded nucleic acid molecule comprising two nucleotide strands. The length of each strand can vary significantly. The term "length" when referring to a double-stranded interfering RNA means that the antisense and sense strands independently have a certain length, including interfering RNA molecules where the sense and antisense strands are connected by a linker molecule. siRNAs have a well-defined structure: a short double strand of RNA with 2-nucleotides 3' overhangs on either end.

RNA interference is a two-step process. During the first step, which is termed the initiation step, input dsRNA is digested into 21-23 nucleotide (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner.

The term "ddRNAi agent" refers to an RNAi agent that is transcribed from a vector. The terms "short hairpin RNA" or "shRNA" refer to an RNA structure having a duplex region and a loop region.

Although the RNA interference effect, which is mediated by small interfering RNA (siRNA) or micro-RNA, has a recognized potential application to human therapy, its application is limited due to the lack of delivery means suitable for human use.

The nucleic acid agents of the present invention can be generated according to any nucleic acid production method known in the art, including both enzymatic syntheses and solid-phase syntheses, as well as using recombinant methods well known in the art.

Equipment and reagents for executing solid-phase synthesis are commercially available from, for example, Applied Biosystems. Any other means for such synthesis may also be employed; the actual synthesis of the nucleic acid agents is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York.

It will be appreciated that nucleic acid agents of the present invention can be also generated using an expression vector as is further described hereinbelow.

Optionally, the nucleic acid agents of the present invention are modified. Nucleic acid agents can be modified using various methods known in the art.

In certain embodiments, the nucleic acid agents are modified either in backbone, internucleoside linkages, or bases, as is known in the art and as described herebelow.

Specific examples of nucleic acid agents useful according to these embodiments of the present invention include oligonucleotides or polynucleotides containing modified backbones or non-natural internucleoside linkages. Examples of oligonucleotides or polynucleotides having modified backbones include those that retain a phosphorus atom in the backbone. Other modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts.

Other non-limiting examples of oligonucleotides or polynucleotides contemplated by the present invention include nucleic acid analogs containing bicyclic and tricyclic nucleoside and nucleotide analogs referred to as "locked nucleic acids," "locked nucleoside analogues," or "LNAs" (see, e.g., U.S. Pat. No. 6,083,482).

Other nucleic acid agents that may be used according to the present invention are those modified in both sugar and the internucleoside linkage, i.e., the backbone of the nucleotide units is replaced with novel groups. The base units are maintained for complementation with the appropriate polynucleotide target. Nucleic acid agents of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine.

The nucleic acid-based agents of the present invention may be produced using standard recombinant and synthetic methods well known in the art. An isolated nucleic acid sequence can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the function of the nucleic acid molecules.

A nucleic acid molecule homolog can be produced using a number of methods known to those skilled in the art. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof.

Polyethylene Glycol

The present invention is based in part on the unexpected discovery that incubation of an aqueous solution comprising polynucleotides with polyethylene glycol (PEG) enhances the capture of the polynucleotide within the lipid-based matrix and affects the release rate of the polynucleotides from the matrix under suitable conditions. As commonly used in the art, poly(ethylene) glycol generally refers to the linear form of poly(ethylene glycol) since these are the most common, commercially available PEG. Linear PEG can be represented by the formula OH—$(CH_2CH_2O)_n$—OH (diol) or mPEG, $CH_3O$—$(CH_2CH_2O)_n OH$, wherein n is the average number of repeating ethylene oxide groups. These PEG compounds are commercially available from, e.g., Sigma-Aldrich in a variety of molecular weights ranging from 1000 to 300,000. Linear PEGs are available as monofunctional or bifunctional forms. PEG's may contain functional reactive groups at either end of the chain and can be homobifunctional (two identical reactive groups) or heterobifunctional (two different reactive groups). For example, heterobifunctional PEG of the formula $_{NH2}$—$(CH_2CH_2O)_n COOH$ are commercially available and are useful for forming PEG derivatives. There are many grades of PEG compounds that are represented by theirs average molecular weight. Pharmaceutical grade PEG is typically in a molecular range of up to 5,000. According to certain typical embodiments, the PEG used according to the teachings of the present invention has a molecular weight of up to 1,000, typically about 2,000-5000.

Additional Components

The matrix composition of the present invention optionally further comprises a free fatty acid. In certain embodiments, the free fatty acid is an omega-6 fatty acid. In other embodiments, the free fatty acid is an omega-9 fatty acid. In another embodiment, the free fatty acid is selected from the group consisting of omega-6 and omega-9 fatty acids. In further embodiments, the free fatty acid has 14 or more carbon atoms. In another embodiment, the free fatty acid has 16 or more carbon atoms. In another embodiment, the free fatty acid has 16 carbon atoms. In another embodiment, the free fatty acid has 18 carbon atoms. In another embodiment, the free fatty acid has 16-22 carbon atoms. In another embodiment, the free fatty acid has 16-20 carbon atoms. In another embodiment, the free fatty acid has 16-18 carbon atoms. In another embodiment, the free fatty acid has 18-22 carbon atoms. In another embodiment, the free fatty acid has 18-20 carbon atoms. In another embodiment, the free fatty acid is linoleic acid. In another embodiment, the free fatty acid is linolenic acid. In another embodiment, the free fatty acid is oleic acid. In another embodiment, the free fatty acid is selected from the group consisting of linoleic acid, linolenic acid, and oleic acid. In another embodiment, the free fatty acid is another appropriate free fatty acid known in the art. In another embodiment, the free fatty acid adds flexibility to the matrix composition. In another embodiment, the free fatty acid slows the release rate, including the in vivo release rate. In another embodiment, the free fatty acid improves the consistency of the controlled release, particularly in vivo. In another embodiment, the free fatty acid is saturated. In another embodiment, incorporation of a saturated fatty acid having at least 14 carbon atoms increases the gel-fluid transition temperature of the resulting matrix composition.

In another embodiment, the free fatty acid is incorporated into the matrix composition.

In another embodiment, the free fatty acid is deuterated. In another embodiment, deuteration of the lipid acyl chains lowers the gel-fluid transition temperature.

Each type of fatty acid represents a separate embodiment of the present invention.

According to certain embodiments, a matrix composition of the present invention further comprises a tocopherol. The tocopherol is, in another embodiment, E307 (α-tocopherol). In another embodiment, the tocopherol is β-tocopherol. In another embodiment, the tocopherol is E308 (γ-tocopherol). In another embodiment, the tocopherol is E309 (δ-tocopherol). In another embodiment, the tocopherol is selected from the group consisting of α-tocopherol, β-tocopherol, γ-tocopherol, and δ-tocopherol. In another embodiment, the tocopherol is incorporated into the matrix composition. Each possibility represents a separate embodiment of the present invention.

The matrix composition of the present invention optionally further comprises physiologically acceptable buffer salts, which are well known in the art. Non-limiting examples of physiologically acceptable buffer salts are phosphate buffers. A typical example of a phosphate buffer is 40 parts NaCl, 1 part KCl, 7 parts $Na_2HPO_4.2H_2O$ and 1 part $KH_2PO_4$. In another embodiment, the buffer salt is any other physiologically acceptable buffer salt known in the art. Each possibility represents a separate embodiment of the present invention.

Release Rates and General Characteristics of the Matrix Compositions

The release time of 90% of the active ingredient for matrix compositions of the present invention under suitable conditions is preferably between 4 days and 6 months. In another embodiment, the release time is between 1 week and 6 months. In another embodiment, the release time is between 1 week and 5 months. In another embodiment, the release time is between 1 week and 5 months. In another embodiment, the release time is between 1 week and 4 months. In another embodiment, the release time is between 1 week and 3 months. In another embodiment, the release time is between 1 week and 2 months. In another embodiment, the release time is between 2 weeks and 6 months. In another embodiment, the release time is between 2 weeks and 5 months. In another embodiment, the release time is between 2 weeks and 4 months. In another embodiment, the release time is between 2 weeks and 3 months. In another embodiment, the release time is between 3 weeks and 6 months. In another embodiment, the release time is between 3 weeks and 5 months. In another embodiment, the release time is between 3 weeks and 4 months. In another embodiment, the release time is between 3 weeks and 3 months. Each possibility represents a separate embodiment of the present invention.

The sustained release period using the compositions of the present invention can be programmed taking into account four major factors: (i) the weight ratio between the polymer and the lipid content, specifically the phospholipid having fatty acid moieties of at least 14 carbons, (ii) the biochemical and/or biophysical properties of the biopolymers and the lipids used; (iii) the ratio between the different lipids used in a given composition and (iv) the incubation time of the nucleic acid agent with polyethylene glycol.

As exemplified herein below, when the matrix is devoid of the lipid portion most of the loaded polynucleotide is released within the first hour, indicating that the lipid mass is essential for graduate release of the polynucleotides. The ratio of total lipids to the polymer in order to achieve lipid saturation can be determined by a number of methods, as described herein. According to certain embodiments, the lipid:polymer weight ratio of a composition of the present invention is between 1:1 and 9:1 inclusive. In another embodiment, the ratio is between 1.5:1 and 9:1 inclusive. In another embodiment, the ratio is between 2:1 and 9:1 inclusive. In another embodiment, the ratio is between 3:1 and 9:1 inclusive. In another embodiment, the ratio is between 4:1 and 9:1 inclusive. In another embodiment, the ratio is between 5:1 and 9:1 inclusive. In another embodiment, the ratio is between 6:1 and 9:1 inclusive. In another embodiment, the ratio is between 7:1 and 9:1 inclusive. In another embodiment, the ratio is between 8:1 and 9:1 inclusive. In another embodiment, the ratio is between 1.5:1 and 5:1 inclusive. Each possibility represents a separate embodiment of the present invention.

In another embodiment for purposes of illustration, in the case wherein the polymer is predominantly 40 KDa PLGA (poly (lactic-co-glycolic acid, 1:1 ratio)), the molar ratio of total lipids to 40 KDa PLGA is typically in the range of 20-100 inclusive. In another embodiment, the molar ratio of total lipids to 40 KDa PLGA is between 20-200 inclusive. In another embodiment, the molar ratio is between 10-100 inclusive. In another embodiment, the molar ratio is between 10-200 inclusive. In another embodiment, the molar ratio is between 10-50 inclusive. In another embodiment, the molar ratio is between 20-50 inclusive. Each possibility represents a separate embodiment of the present invention.

Implants and Other Pharmaceutical Compositions

The matrix composition of the present invention can be molded to the form of an implant, following removal of the organic solvents and water. The removal of the solvents is typically performed by evaporation under a specific temperature between room temperature and 90° C., followed by vacuum.

In another embodiment, the implant is homogeneous. In another embodiment, the implant is manufactured by a process comprising the step of freeze-drying the material in a mold. Each possibility represents a separate embodiment of the present invention.

According to additional embodiments, the present invention provides an implant comprising a matrix composition comprising a nucleic acid based agent of the present invention.

The present invention further provides a process of creating an implant from a composition of the present invention comprising the steps of (a) creating a matrix composition according to the method of the present invention in the form of a bulk material; (b) transferring the bulk material into a mold or solid receptacle of a desired shaped; (c) freezing the bulk material; and (d) lyophilizing the bulk material.

In additional embodiments, the present invention provides a pharmaceutical composition comprising a matrix composition of the present invention. According to certain embodiments, the pharmaceutical composition further comprises additional pharmaceutically acceptable excipients. In additional embodiments, the pharmaceutical composition is in a parenterally injectable form. In other embodiments, the pharmaceutical composition is in an infusible form. In yet additional embodiments, the excipient is compatible for injection. In further embodiments, the excipient is compatible for infusion. Each possibility represents a separate embodiment of the present invention.

Use of the matrix composition of the present invention for the production of micro-vesicles, ranging from 100 nm to 50 m is also within the scope of the present invention.

According to certain embodiments, the matrix composition of the present invention is in the form of microspheres, following removal of the organic solvents and water. In other embodiment, the microspheres are homogeneous. According to certain embodiments, the microspheres are manufactured by a process comprising the step of spray-drying. Each possibility represents a separate embodiment of the present invention.

In another embodiment, the present invention provides microspheres made of a matrix composition of the present invention. In another embodiment, the present invention provides a pharmaceutical composition comprising microspheres of the present invention and a pharmaceutically acceptable excipient. Each possibility represents a separate embodiment of the present invention.

In another embodiment, the particle size of microspheres of the present invention is approximately 500-2000 nm. In another embodiment, the particle size is about 400-2500 nm. In another embodiment, the particle size is about 600-1900 nm. In another embodiment, the particle size is about 700-1800 nm. In another embodiment, the particle size is about 500-1800 nm. In another embodiment, the particle size is about 500-1600 nm. In another embodiment, the particle size is about 600-2000 nm. In another embodiment, the particle size is about 700-2000 nm. In another embodiment, the particles are of any other size suitable for pharmaceutical administration. Each possibility represents a separate embodiment of the present invention.

Methods of Making Matrix Compositions of the Present Invention

The present invention further provides a process for producing a matrix composition for sustained release of a nucleic acid agent comprising:

(a) mixing into a first volatile organic solvent (i) a biodegradable polymer and (ii) a first lipid component comprising at least one lipid having a polar group;

(b) mixing polyethylene glycol into a water-based solution of the nucleic acid agent;

(c) mixing the solution obtained in step (b) with a second volatile organic solvent and a second lipid component comprising at least one phospholipid having fatty acid moieties of at least 14 carbons;

(d) mixing the solutions obtained in steps (a) and (c) to form a homogeneous mixture; and (e) removing the volatile solvents and water, Thereby producing a homogeneous polymer-phospholipids matrix comprising the nucleic acid agent.

According to certain typical embodiments, the method comprises the steps of (a) mixing into a first volatile organic solvent: (i) a biodegradable polyester and (ii) sterol; (b) mixing into a different container containing nucleic acid based drug in water-based solution comprising polyethylene glycol (1) a phosphatidylcholine in a second water-miscible volatile organic solvent and/or (2) a phosphatidylethanolamine in the water-miscible volatile organic solvent and (3) mixing the resulted solution in a given temperature (4) optionally precipitating the resulted material by centrifugation or by freeze-drying and optionally re-suspending the precipitate in a selected volatile solvent; and (c) mixing and homogenizing the products resulting from steps (a) and (b).

According to certain embodiments, the biodegradable polymer is selected from the group consisting of PLGA, PGA PLA or combinations thereof. In other embodiments, the biodegradable polyester is any other suitable biodegradable polyester known in the art. According to yet additional embodiments, the biodegradable polymer is a polyamine. Mixing the polymer with the at least one lipid having a polar group (non-limiting example being sterol, particularly cholesterol), within the first organic solvent, is typically performed at room temperature. Optionally, α- and/or γ-tocopherol are added to the solution. A lipid-polymer matrix is formed.

The water-based solution containing the at least one nucleic-acid based agent and polyethylene glycol is mixed, typically under stirring, with the second volatile organic solvent (selected from the group consisting of, but not limited to N-methylpyrrolidone, ethanol, methanol, ethyl acetate or combination thereof) comprising the at least one phospholipid. According to certain embodiments, the phospholipid is phosphocholine or phosphatidylcholine or derivatives thereof. According to other embodiments, the phospholipid is phosphatidylcholine or a derivative thereof. According to additional embodiments, the second volatile organic solvent comprises combination of phosphatidylcholine, phosphatidylcholine or derivatives thereof. According to certain embodiments, the phosphocholine or phosphatidylcholine or derivatives thereof is present at 10-90% mass of all lipids in the matrix, i.e. 10-90 mass % of phospholipids, sterols, ceramides, fatty acids etc. According to other embodiments, the phosphatidylethanolamine is present as 10-90 mass % of all lipids in the matrix.

According to yet other embodiments, phosphocholine or phosphatidylcholine derivative or their combination at different ratios with phosphatidylethanolamine are mixed in the organic solvent prior to its addition to the water based solution comprising the nucleic acids and PEG.

In another embodiment, the phosphatidylethanolamine is also included in the first lipid component.

In another embodiment, the mixture (a) containing the organic solvent is homogenized prior to mixing it with the mixture containing the water-miscible organic solvent. In another embodiment, the mixture (c) containing the water-miscible organic solvent is homogenized prior to mixing it with the mixture containing another type of organic solvent. In another embodiment, the polymer in the mixture of step (a) is lipid saturated. In another embodiment, the matrix composition is lipid saturated. Typically, the polymer and the phosphatidylcholine are incorporated into the matrix composition. In another embodiment, the active agent as well is incorporated into the matrix composition. In another embodiment, the matrix composition is in the form of a lipid-saturated matrix whose shape and boundaries are determined by the biodegradable polymer. Each possibility represents a separate embodiment of the present invention.

In another embodiment, the phosphatidylethanolamine has saturated fatty acid moieties. In another embodiment, the fatty acid moieties have at least 14 carbon atoms. In another embodiment, the fatty acid moieties have 14-18 carbon atoms. Each possibility represents a separate embodiment of the present invention.

In another embodiment, the phosphatidylcholine has saturated fatty acid moieties. In another embodiment, the fatty acid moieties have at least 14 carbon atoms. In another embodiment, the fatty acid moieties have at least 16 carbon atoms. In another embodiment, the fatty acid moieties have 14-18 carbon atoms. In another embodiment, the fatty acid moieties have 16-18 carbon atoms. Each possibility represents a separate embodiment of the present invention.

In another embodiment, the molar ratio of total lipids to polymer in the non-polar organic solvent is such that the polymer in this mixture is lipid-saturated. In another embodiment for purposes of illustration, in the case wherein the polymer is predominantly 50 KDa PLGA (poly (lactic-co-glycolic acid, 1:1 ratio)), the molar ratio of total lipids to 50 KDa PLGA is typically in the range of 10-50 inclusive. In another embodiment, the molar ratio of total lipids to 50 KDa PLGA is between 10-100 inclusive. In another embodiment, the molar ratio is between 20-200 inclusive. In another embodiment, the molar ratio is between 20-300 inclusive. In another embodiment, the molar ratio is between 30-400 inclusive. Each possibility represents a separate embodiment of the present invention.

Each of the components of the above method and other methods of the present invention is defined in the same manner as the corresponding component of the matrix compositions of the present invention.

In another embodiment, step (a) of the production method further comprises adding to the volatile organic solvent, typically non-polar solvent, a phosphatidylethanolamine. In another embodiment, the phosphatidylethanolamine is the same phosphatidylethanolamine included in step (c). In another embodiment, the phosphatidylethanolamine is a different phosphatidylethanolamine that may be any other phosphatidylethanolamine known in the art. In another embodiment, the phosphatidylethanolamine is selected from the group consisting of the phosphatidylethanolamine of step (c) and a different phosphatidylethanolamine. Each possibility represents a separate embodiment of the present invention.

In another embodiment, step (c) of the production method further comprises adding to the volatile organic solvent, typically a water-miscible solvent, a phospholipid selected from the group consisting of a phosphatidylserine, a phosphatidylglycerol, a sphingomyelin, and a phosphatidylinositol.

In another embodiment, step (c) of the production method further comprises adding to the water-miscible volatile organic solvent a sphingolipid. In another embodiment, the sphingolipid is ceramide. In another embodiment, the sphingolipid is a sphingomyelin. In another embodiment, the sphingolipid is any other sphingolipid known in the art. Each possibility represents a separate embodiment of the present invention.

In another embodiment, step (c) of the production method further comprises adding to the water-miscible, volatile organic solvent an omega-6 or omega-9 free fatty acid. In another embodiment, the free fatty acid has 16 or more carbon atoms. Each possibility represents a separate embodiment of the present invention.

Upon mixing, a homogenous mixture is formed, since the polymer is lipid-saturated in the mixture of step (a). In another embodiment, the homogenous mixture takes the form of a homogenous liquid. In another embodiment, upon freeze-drying or spray-drying the mixture, vesicles are formed. Each possibility represents a separate embodiment of the present invention.

In another embodiment, the production method further comprises the step of removing the solvent and water present in the product of step (d). In certain embodiments, the solvent and eater removal utilizes atomization of the mixture. In other embodiments, the mixture is atomized into dry, heated air. Typically, atomization into heated air evaporates all water immediately, obviating the need for a subsequent drying step. In another embodiment, the mixture is atomized into a water-free solvent. In another embodiment, the liquid removal is performed by spray drying. In another embodiment, the liquid removal is performed by freeze drying. In another embodiment, the liquid removal is performed using liquid nitrogen. In another embodiment, the liquid removal is performed using liquid nitrogen that has been pre-mixed with ethanol. In another embodiment, the liquid removal is performed using another suitable technique known in the art. Each possibility represents a separate embodiment of the present invention.

In another embodiment, a method of the present invention further comprises the step of vacuum-drying the composition. In another embodiment, the step of vacuum-drying is performed following the step of evaporation. Each possibility represents a separate embodiment of the present invention.

In another embodiment, a method of the present invention further comprises the step of evaporating the organic volatile solvent by heating the product of step (d). The heating is continuing until the solvent is eliminated and in a typical temperature between room temperature to 90° C. In another embodiment a step of vacuum-drying is performed following the step of evaporating. Each possibility represents a separate embodiment of the present invention.

Lipid Saturation and Techniques for Determining Same

"Lipid saturated," as used herein, refers to saturation of the polymer of the matrix composition with phospholipids in combination with a nucleic acid agent and optionally targeting moiety present in the matrix, and any other lipids that may be present. As described herein, matrix compositions of the present invention comprise, in some embodiments, phospholipids other than phosphatidylcholine. In other embodiments, the matrix compositions may comprise lipids other than phospholipids. The matrix composition is saturated by whatever lipids are present. "Saturation" refers to a state wherein the matrix contains the maximum amount of lipids of the type utilized that can be incorporated into the matrix. Methods for determining the polymer:lipid ratio to attain lipid saturation and methods of determining the degree of lipid saturation of a matrix are known to a person skilled in the art. Each possibility represents a separate embodiment of the present invention.

According to certain typical embodiments, the final matrix composition of the present invention is substantially free of water in contrast to hitherto known lipid-based matrices designed for nucleic acids delivery. In other words, even when the active ingredients are initially dissolved in an aqueous solution all the solvents are removed during the process of preparing the lipid polymer compositions. The substantially absence of water from the final composition protects the bioactive nucleic acid from degradation or chemical modification, particularly from enzyme degradation. Upon application of the composition to an hydrous biological environment, the outer surface of the matrix composition contacts the biological liquids while the substantially water free inner part protects the remaining active ingredient thus enabling sustained release of undamaged active ingredient.

According to certain embodiments, the term "substantially free of water" refers to a composition containing less than 1% water by weight. In another embodiment, the term refers to a composition containing less than 0.8% water by weight. In another embodiment, the term refers to a composition containing less than 0.6% water by weight. In another embodiment, the term refers to a composition containing less than 0.4% water by weight. In another embodiment, the term refers to a composition containing less than 0.2% water by weight. In another embodiment, the term refers to the absence of amounts of water that affect the water-resistant properties of the matrix.

In another embodiment, the matrix composition is essentially free of water. "Essentially free" refers to a composition comprising less than 0.1% water by weight. In another embodiment, the term refers to a composition comprising less than 0.08% water by weight. In another embodiment, the term refers to a composition comprising less than 0.06% water by weight. In another embodiment, the term refers to a composition comprising less than 0.04% water by weight. In another embodiment, the term refers to a composition comprising less than 0.02% water by weight. In another embodiment, the term refers to a composition comprising less than 0.01% water by weight. Each possibility represents a separate embodiment of the present invention.

In another embodiment, the matrix composition is free of water. In another embodiment, the term refers to a composition not containing detectable amounts of water. Each possibility represents a separate embodiment of the present invention.

The process of preparing the matrix of the present invention comprises only one step where an aqueous solution is used. This solution is mixed with organic volatile solvent, and all the liquids are removed thereafter. The process of the present invention thus enables lipid saturation. Lipid saturation confers upon the matrix composition ability to resist bulk degradation in vivo; thus, the matrix composition exhibits the ability to mediate extended release on a scale of several weeks or months.

In another embodiment, the matrix composition is dry. "Dry" refers, in another embodiment, to the absence of detectable amounts of water or organic solvent.

In another embodiment, the water permeability of the matrix composition has been minimized. "Minimizing" the water permeability refers to a process of producing the matrix composition mainly in organic solvents, as described herein, in the presence of the amount of lipid that has been determined to minimize the permeability to penetration of added water. The amount of lipid required can be determined by hydrating the vesicles with a solution containing tritium-tagged water, as described herein.

In another embodiment, "lipid saturation" refers to filling of internal gaps (free volume) within the lipid matrix as defined by the external border of the polymeric backbone. The gaps are filled with the phospholipids in combination with any other types of lipids, nucleic acid agent and optionally targeting moiety present in the matrix, to the extent that additional lipid moieties can no longer be incorporated into the matrix to an appreciable extent.

Zero-order release rate" or "zero order release kinetics" means a constant, linear, continuous, sustained and controlled release rate of the nucleic acid agent from the polymer matrix, i.e. the plot of amounts of the nucleic acid agent released vs. time is linear.

Therapeutic Applications of Nucleic Acid Agents

The present invention also relates to a variety of applications in which it is desired to modulate, e.g., one or more target genes, viral replication of a pathogenic virus, etc., in a whole eukaryotic organism, e.g., a mammal or a plant; or portion thereof, e.g., tissue, organ, cell, etc. In such methods, an effective amount of a nucleic acid active agent is administered to the host or introduced into the target cell. The term "effective amount" refers to a dosage sufficient to modulate expression of the target viral gene(s), as desired, e.g., to achieve the desired inhibition of viral replication. As indicated above, in certain embodiments of this type of application, the subject methods are employed to reduce expression of one or more target genes in the host in order to achieve a desired therapeutic outcome.

When the target gene is a viral gene, e.g., when inhibition of viral replication is desired, the target viral gene can be from a number of different viruses. Representative viruses include, but are not limited to: HBV, HCV, HIV, influenza A, Hepatitis A, picornaviruses, alpha-viruses, herpes viruses, and the like.

The methods described herein are also suitable for inhibiting the expression of a target gene in a tumor cell. The present invention relates to any type of cancer including solid tumors and non-solid tumors. The solid tumors are exemplified by, but are mot limited to, CNS tumors, liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas. Non-solid tumors include lymphoproliferative disorders including leukemias and lymphomas. Each possibility represents a separate embodiment of the present invention.

Another application in which the subject methods find use is the elucidation of gene function by a functional analysis of eukaryotic cells, or eukaryotic non-human organisms, preferably mammalian cells or organisms and most preferably human cells, e.g. cell lines such as HeLa or 293, or rodents, e.g. rats and mice. By transfection with vector molecules which are homologous to a predetermined target gene encoding a suitable RNA molecule, a specific knockdown phenotype can be obtained in a target cell, e.g. in cell culture or in a target organism.

The present invention is also useful to produce plants with improved characteristics including but not limited to decreased susceptibility to biotic as well as abiotic stress, insect infestation, pathogen infection, and improved agricultural characteristics including ripening characteristics. Any gene or genes that may be detrimental in the agricultural community could be a potential target or targets of such specially selected nucleic acids.

EXAMPLES

Example 1

Platform Technology for Production of Drug Carrier Compositions for the Delivery of Nucleic Acid Based Agents I. Preparation of First Solution A Polymer (for example, PLGA, PGA, PLA, or a combination thereof) and a sterol (e.g. cholesterol) and/or alpha- or gamma tocopherol are mixed in a volatile organic solvent (e.g. ethyl acetate with/without chloroform). The entire process is performed at room temperature. A lipid-polymer matrix is thus obtained.

II. Preparation of Second Solution

At least one nucleic-based agent is dissolved in water and polyethylene glycol (PEG) 1,000-8000, typically PEG 5,000 is added. The resulted solution is mixed, typically under stirring, with a volatile organic solvent (typically N-methylpyrrolidone, ethanol, methanol, ethyl acetate or combination thereof) comprising:

A phosphocholine or phosphatidylcholine derivative, e.g. deuterated 1,2-distearoyl-sn-glycero-3-phosphocholine (DSPC) or dioleoyl-phosphatidylcholine (DOPC), Dipalmitoyl-phosphatidylcholine (DPPC), Dimyristoyl-phosphatidylcholine (DMPC), dioleoyl-phosphatidylcholine (DOPC), 1-palmitoyl-2-oleoyl-phosphatidylcholine, present as 10-90 mass % of all lipids in the matrix, i.e. 10-90 mass % of phospholipids, sterols, ceramides, fatty acids etc;

Optionally, phosphatidylethanolamine—e.g. dimethyldimyristoyl phosphatidylethanolamine (DMPE) or dipalmitoyl-phosphatidylethanolamine (DPPE)—present as 10-90 mass % of all lipids in the matrix;

Optionally, phosphocholine or phosphatidylcholine derivative or their combination at different ratios of phosphatidylethanolamine, mixed in the organic solvent prior to its addition of the NA drug water based solution;

Optionally, cationic lipid is included as 0.1-10 mol % of all lipids in the matrix;

Optionally, 0.1-15 mass % of a free fatty acid, e.g. linoleic acid (LN), or oleic acid (OA), as 0.1-10 mass % of all lipids in the matrix;

The mixture is homogenized, sonicated or used for coating the surface of medical devices. Typically the entire process is conducted at room temperature, but higher temperatures of up to about 90° C. can be used, typically when highly saturated lipids are used.

III. Mixing the Polymer with the Nucleic Acids-PEG Mixture

The second suspension (or solution) is added to the first solution under stirring. Stirring is continued for up to about 5 h. The entire process is performed at room temperature and up to 90° C., all according to the specific formulation, the nature of the lipids in use and the specific nucleic acid agent. The resulting mixture should be homogenous, but can also be slightly turbid.

IV. Removal of the Solvents

When coating of surfaces is performed; the suspension from stage III is mixed with the particles or devices to be coated followed by evaporation of the volatile organic solvents. The entire coating process is performed at a temperature of about 30-90° C.

The solution from stage III may be optionally atomized into dry, heated air.

Alternatively the solution from stage III is atomized into water based solution, which may contain carbohydrates, or atomized into ethanol covered by liquid nitrogen or only liquid nitrogen without ethanol, after which the nitrogen and/or ethanol (as above) are evaporated.

V. Vacuum Drying

The matrix composition, coated particles and coated devices are vacuum-dried. All organic solvent and water residues are removed. The lipid-based matrix comprising the nucleic acid agent is ready for storage.

Example 2

Preparation of a Matrix Comprising Nucleic Acids without PEG

Matrix Preparation
Stock Solutions:
Stock solution 1 (SS1): PLGA 75/25, 300 mg/ml in ethyl acetate (EA).
Stock solution 2 (SS2): Cholesterol (CH), 30 mg/ml in EA.
Stock solution 3 (SS3): DPPC, 300 mg/ml in Methanol:EA (3:1 v/v).
Single strand DNA oligonucleotides (ssDNA) (23 mer, having the sequence CCATCAACGACCCCTTCATGGAC (SEQ ID NO:1) marked with FAM (fluorescence tagging probe) at the 5' end, 0.5 mM in DDW.
Solution A was obtained by mixing 0.2 volume of SS1 with 1 volume of SS2 (PLGA 50 mg/ml, CH 25 mg/ml).
Solution B was obtained by mixing SS3 and SS4 at 1:1 volume to volume ratio by vortex.
Solution AB was obtained by mixing 1 volume of solution B with 1.5 volumes of solution A by vortex and incubating the mixture at 45° C. for 5 minutes.
To one volume of the AB solution one volume of MetOH:DDW (v/v) was added, followed by vortex and incubation at 45° C. for 10 min (the solution became uniform and milky).

Coating 100 mg of commercial artificial bone substitute (tricalcium phosphate particles, TCP) were coated with 0.25 ml of the matrix solution (solution AB).
The solvents were evaporated by incubation at 45° C. for 1 h of until no liquid is visualized, followed by overnight vacuum.

Example 3

Release of ssDNA from the Matrix Composition Prepared without PEG

TCP particles coated with the matrix comprising the FAM-labeled ssDNA prepared as described in example 2 hereinabove were hydrated with water and incubated at 37° C. After 1 h, the water were collected and replaced with fresh water. This procedure was daily repeated for 23 days. Release of the oligonucleotides into the collected water samples was evaluated by measuring the FAM (5 carboxy-fluorescein) fluorescence by quantitative fluorimetry. (Excitation wavelength—485 nm, Emission wavelength—520 nm). The concentration of the ssDNA released was measured according to a standard curve plotted (Fluorescence vs. oligonucleotide concentration, FIG. 1). A linear standard curve was obtained in the range of 0.05-25 pmole/μl. Percentage of the oligonucleotide released was normalized to the estimated amount of the oligonucleotides loaded into the matrix.

Figure 2:
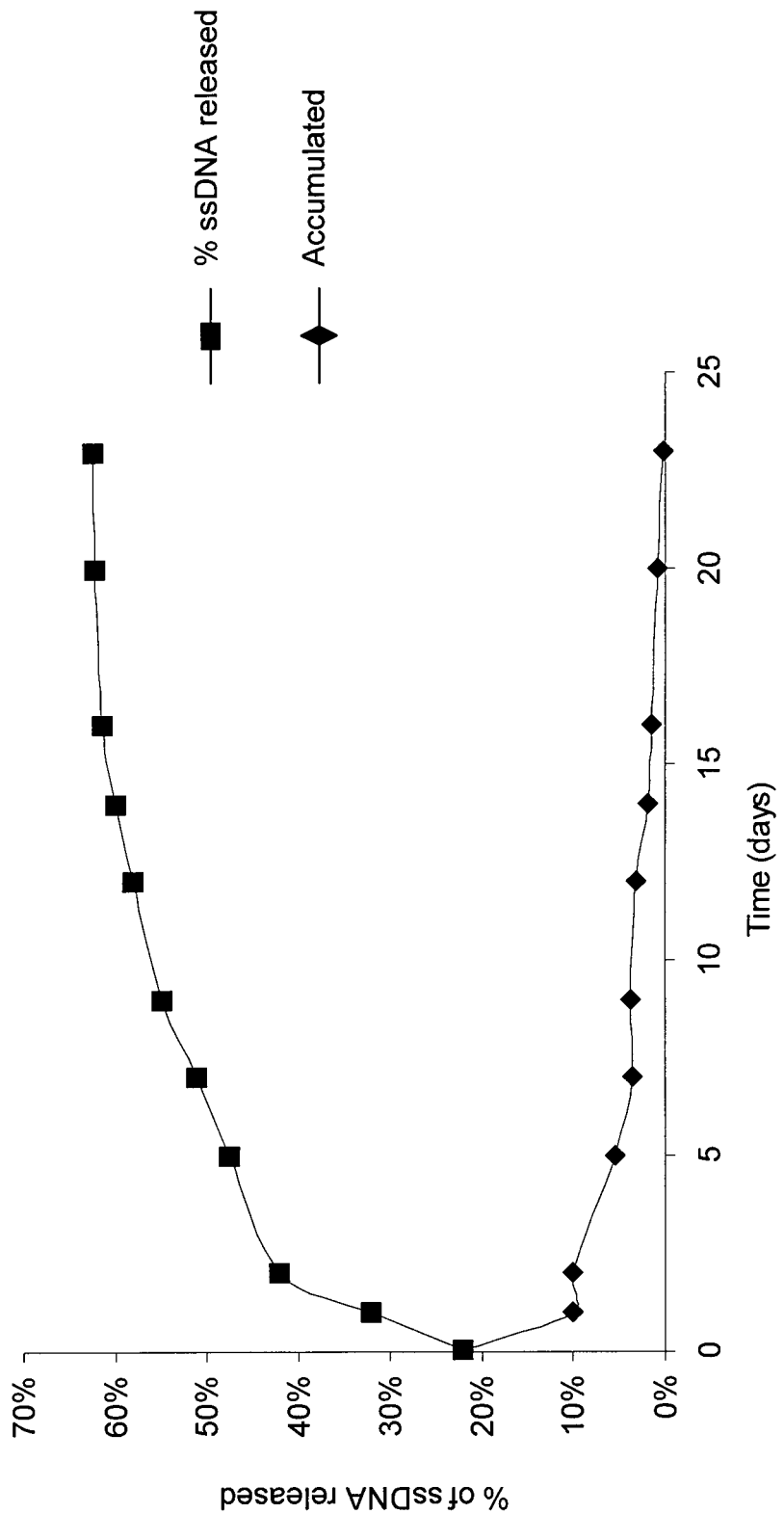

FIG. 2 shows that after 1 hour, about 20% of the loaded ssDNA are released into the water. Thus, this figure clearly demonstrates that the absence of PEG in the oligonucleotide solution negatively affect the amount of ssDNA loaded into the fatty matrix. Thereafter, in the next two days similar amount was released (~10%). From day 5 until day 16, a zero order release of the ssDNA was observed; in average 1-1.8% of the accumulated ssDNA was released every day. From day 16 there was a decrease in the release of the ssDNA until day 23 when the ssDNA concentration in the sample was under the detection limit.

Figure 3B:
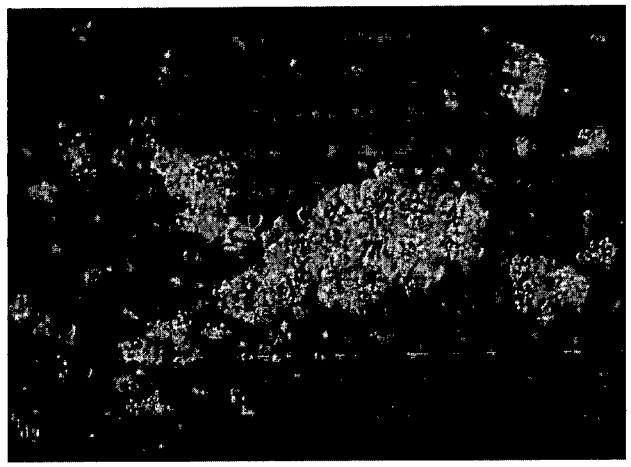
FIGS. 3A and 3B represents light microscopy (X400) pictures of lipid vesicles released following hydration of ssDNA from a matrix composition described in example 2.
Figure 3A:
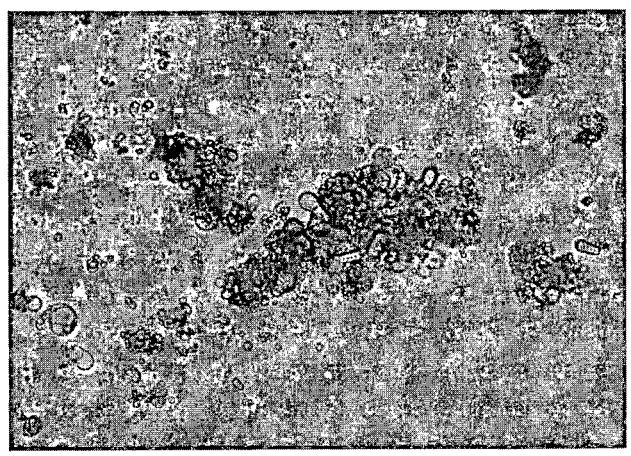

Samples were also examined under light microscopy (×400). As shown in FIG. 3A there was a typical type of lipid vesicles released into the medium following hydration. FIG. 3B shows a green fluorescence emission from the same vesicles indicating that these vesicles contained the florescence probe.

Example 4

Testing the Functionality of the Released Oligonucleotides

The ssDNA loaded into the matrix (having the nucleic acid sequence set forth in SEQ ID NO:1) was designed as a forward primer to amplify fragment of the murine housekeeping gene GapDH. Reverse primer complimentary to the gene was also prepared, consisting of the nucleic acid sequence GGAT-GACCTTGCCCACAGCCTTG (SEQ ID NO:2). After the concentration of the released ssDNA was evaluated, 100 pmole of the released oligonucleotides from different time points were taken for a PCR reaction. cDNA derived from mouse spleen was used as a template. The oligonucleotides released from the matrix and the reverse primer were used to amplify a GapDH fragment with an expected size of about 500 bp. The PCR reaction was performed using ReadyMix™ (Sigma) components.

Figure 4:
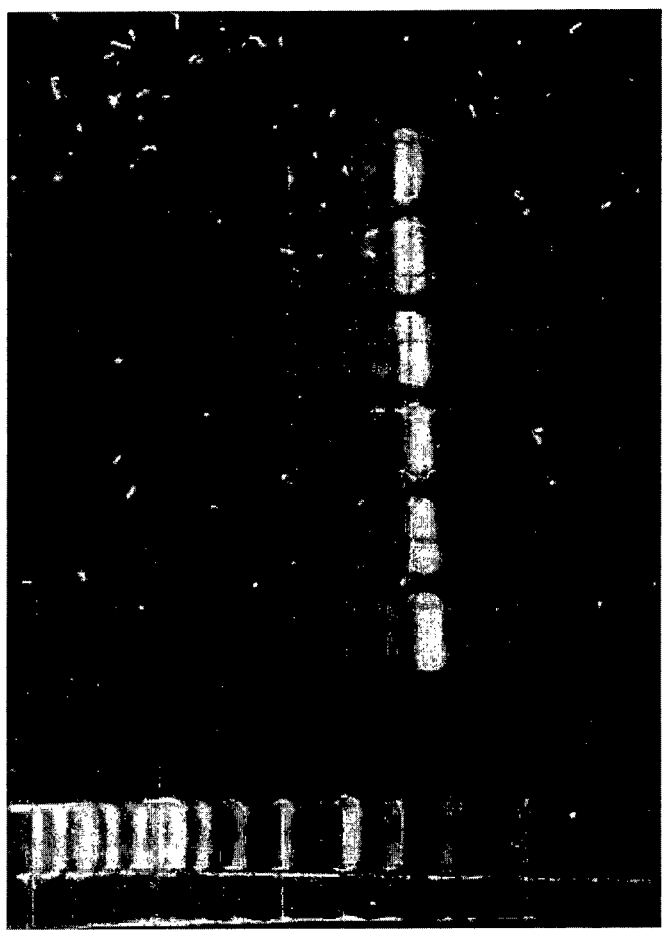
FIG. 4 shows an agarose gel of PCR products amplified with the ssDNA released from the matrix composition.

FIG. 4 shows agarose gel of the PCR products. The expected 500 bp fragment was obtained, confirming that the ssDNA released at all time points tested were active and capable of amplifying the correct gene fragment.

Figure 5:
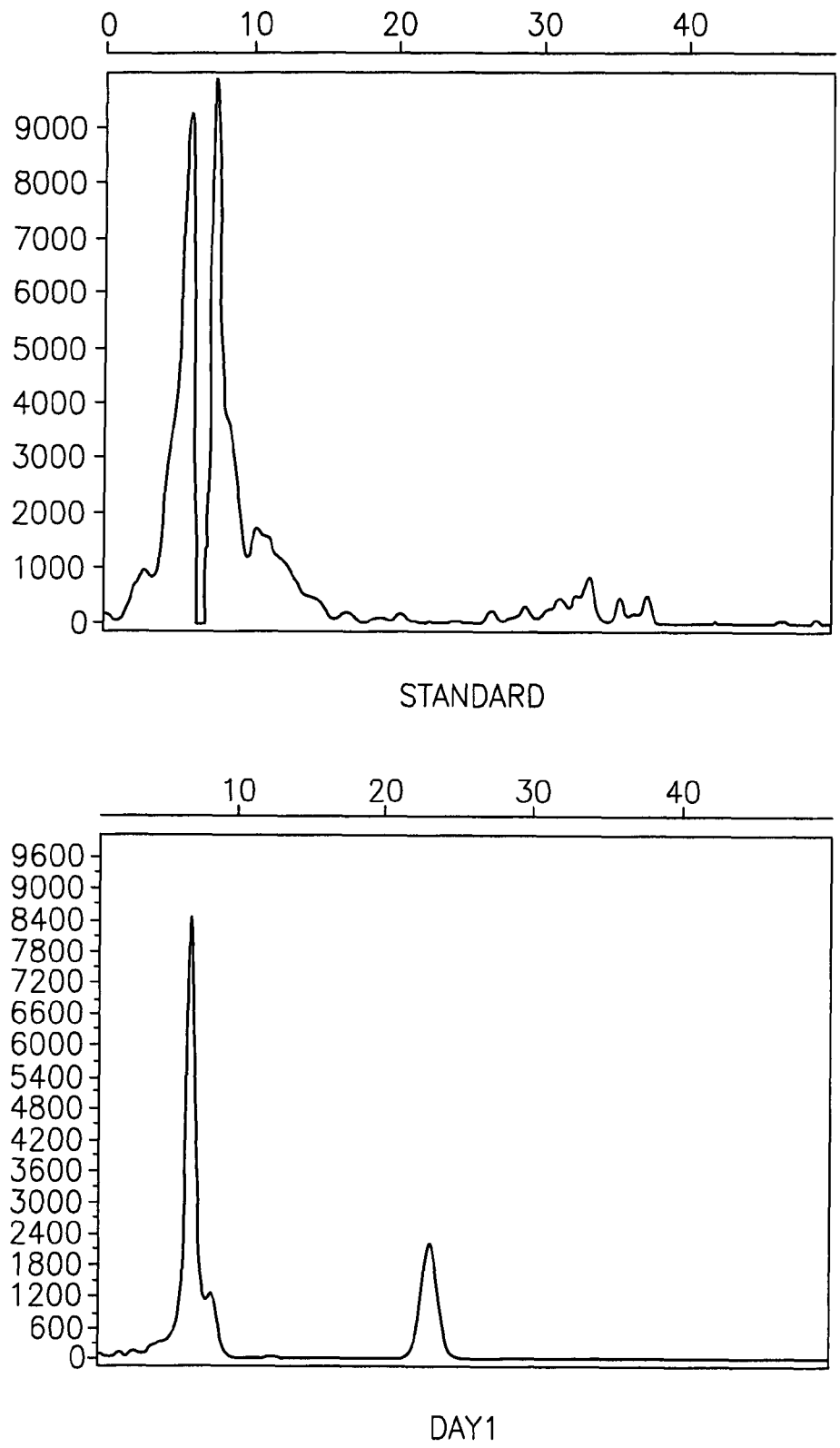
FIG. 5 shows the size of ssDNA released from the matrix composition measured by GeneScan analysis.
Figure 5:
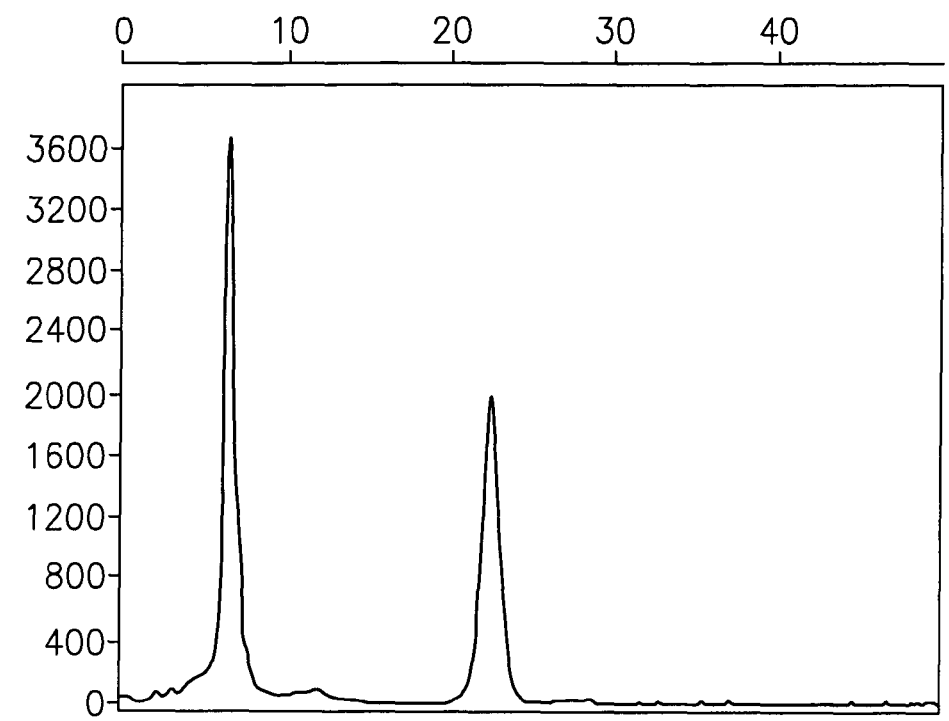
Figure 5:
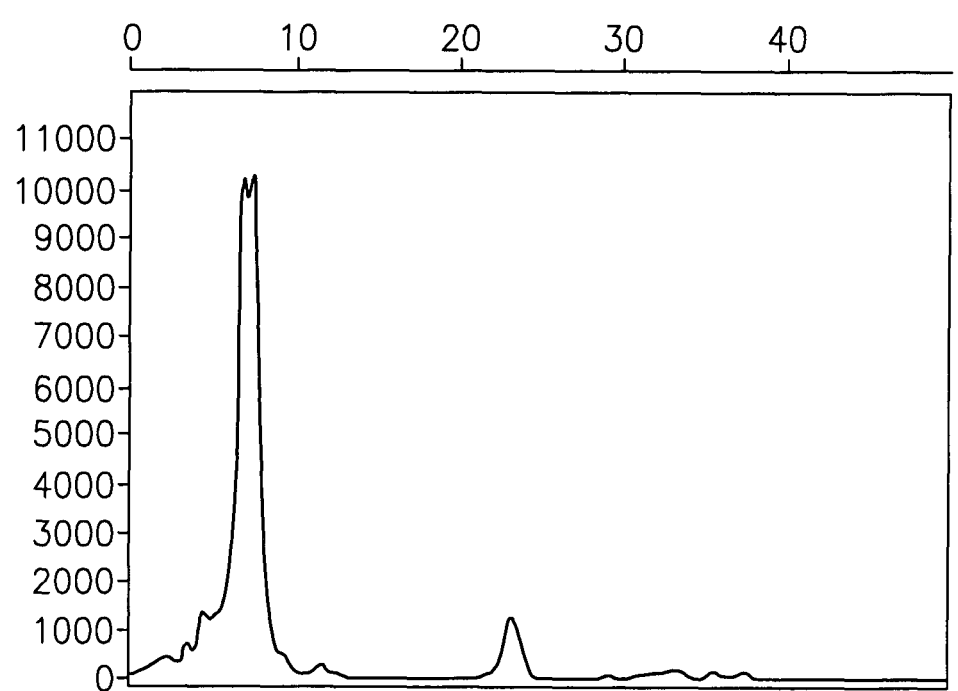
Figure 5:
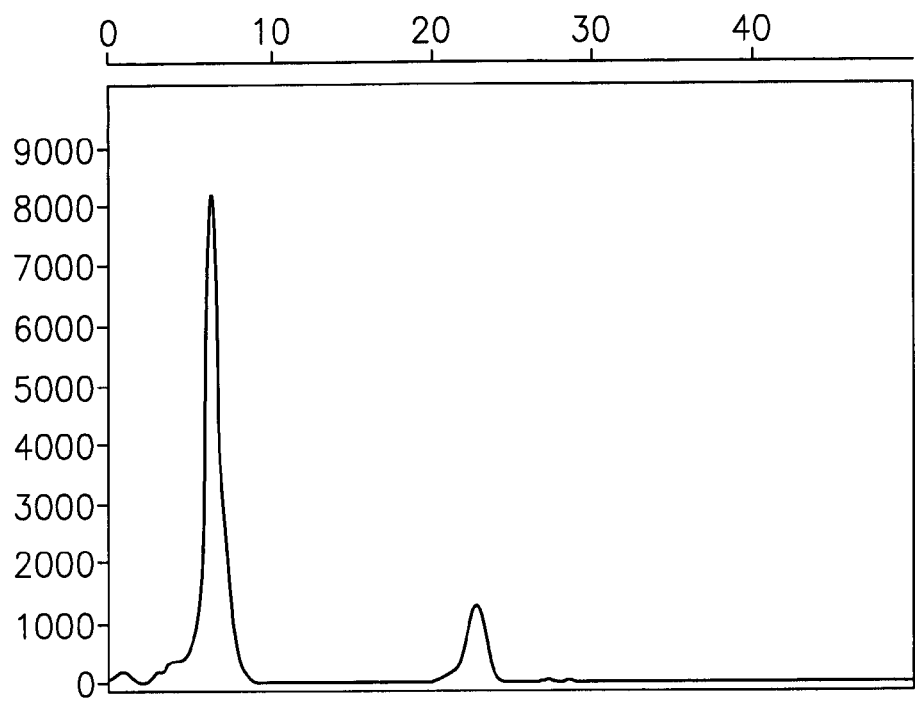
Figure 5:
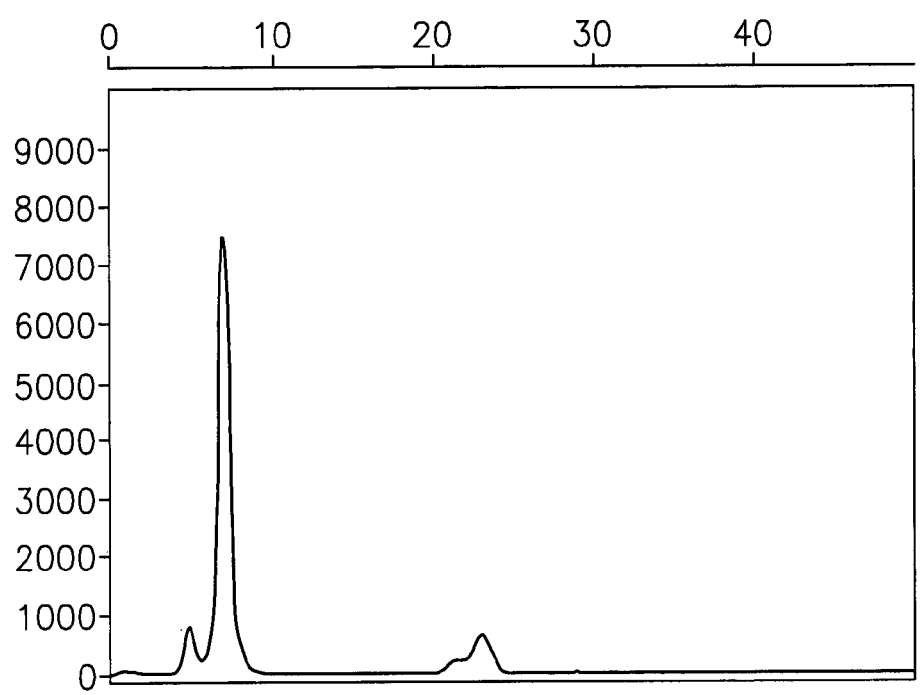
Figure 5:
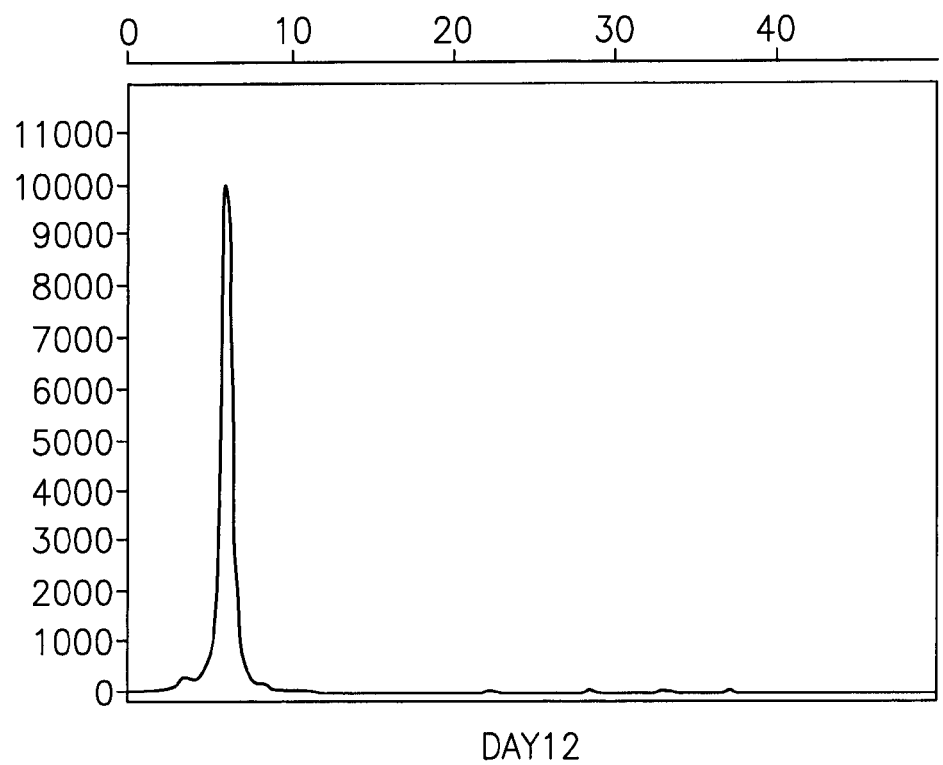
Figure 5:
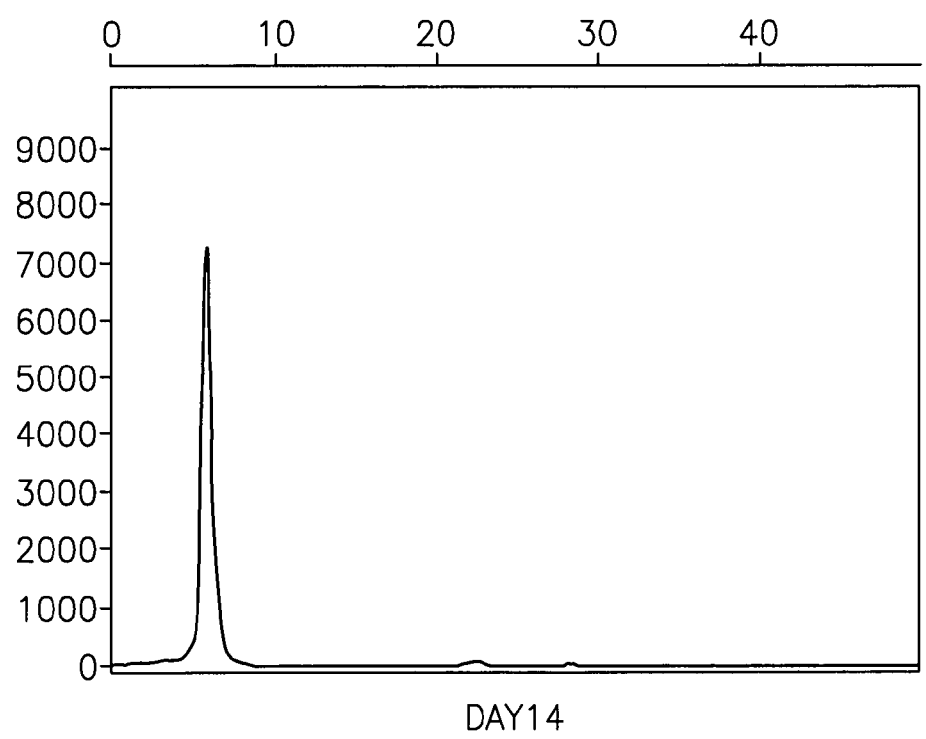
Figure 5:
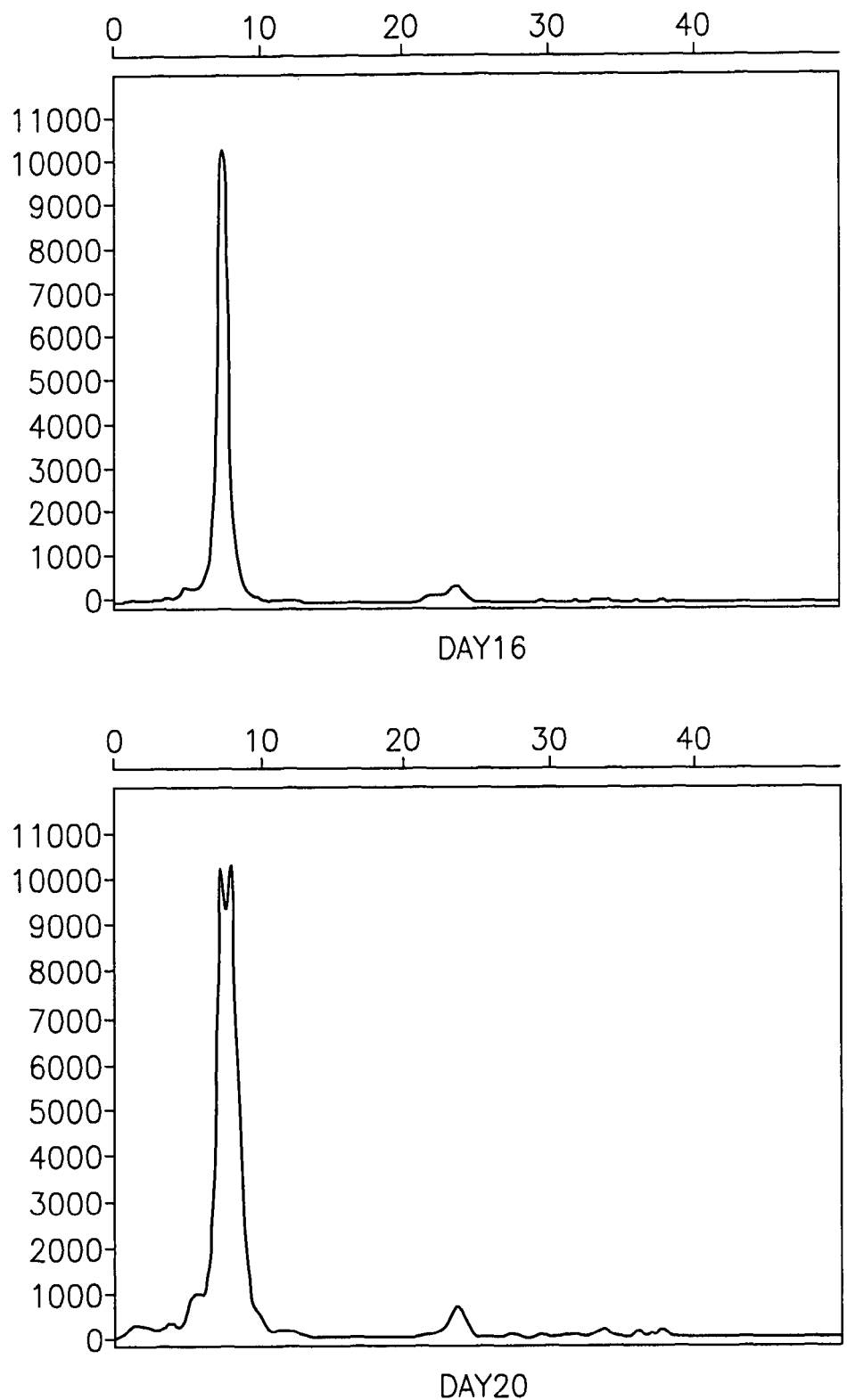

The size of the ssDNA released at the several time points was sent to size evaluation by GeneScan analysis. Samples of ssDNA released after 1, 2, 5, 7, 9, 12, 14, 16 and 20 days were tested. In all samples except those obtained at 14 and 16 days intact oligonucleotides with the size of 23 bp were detected (FIG. 5). The differences in the peak intensities are due to the concentration of the ssDNA in the sample and the quality of precipitation of the DNA from the released complexes. The first observed peak is probably due to the purity of the oligo (it was cleaned by desalting).

Example 5

Preparation of a Matrix Comprising Nucleic Acids with PEG

Matrix Preparation
Stock Solutions:
Stock solution 1 (SS1): PLGA 75/25, 300 mg/ml in ethyl acetate (EA).
Stock solution 2 (SS2): Cholesterol (CH), 30 mg/ml in EA.
Stock solution 3a (SS3a): Single strand DNA oligo (23 mer, having the nucleic acid sequence set forth in SEQ ID NO:1), labeled with FAM at the 5 prime, 0.5 mM in DDW.
Stock solution 3b (SS3b): Polyethylene glycol 8000 (PEG 8000) dissolved in Stock solution 3a (PEG final concentration 250 mg/ml).

Stock solution 3c (SS3c): Stock solution 3b diluted ×10 into MeOH:EA solution (v/v); (ssDNA 0.05 mM; PEG 25 mg/ml).

Solution A was obtained by mixing 0.2 volume of SS1 with 1 volume of SS2 (PLGA 50 mg/ml, CH 25 mg/ml).

Solution B contained phospholipids (DPPC, DMPC, DSPC or DPPC/DPPE 9:1 w/w) dissolved in SS3c, comprising the ssDNA and PEG.

Solution AB was obtained by mixing 1 volume of solution B with 1.5 volumes of solution A by vortex and incubating the mixture at 45° C. for 5 minutes.

Coating 100 mg of commercial artificial bone substitute (tricalcium phosphate particles, TCP) were coated with 0.25 ml of the matrix solution (solution AB). The solvents were evaporated by incubation at 45° C. for 1 h of until no liquid is visualized, followed by overnight vacuum.

Example 6

Release of ssDNA from the Matrix Prepared with PEG

TCP particles coated with the matrix comprising the FAM-labaled ssDNA prepared as described in example 5 above (including incubation of the ssDNA with PEG) were hydrated with water and incubated at 37° C.

After 1 h, the water were collected and replaced with fresh water. This procedure was daily repeated for 40 days. Release of the oligonucleotides into the collected water samples was evaluated by measuring the FAM fluorescence as described in Example 3 hereinabove.

The effect of the duration of the incubation time of ssDNA with PEG on the release of ssDNA from the coated particles was also examined:

Stock solution 3b (PEG 8,000 dissolved in water solution of the ssDNA) was diluted into MeOH/EA after one hour of incubation (short incubation) and after 18 hours of incubation (long incubation).

Figure 6:
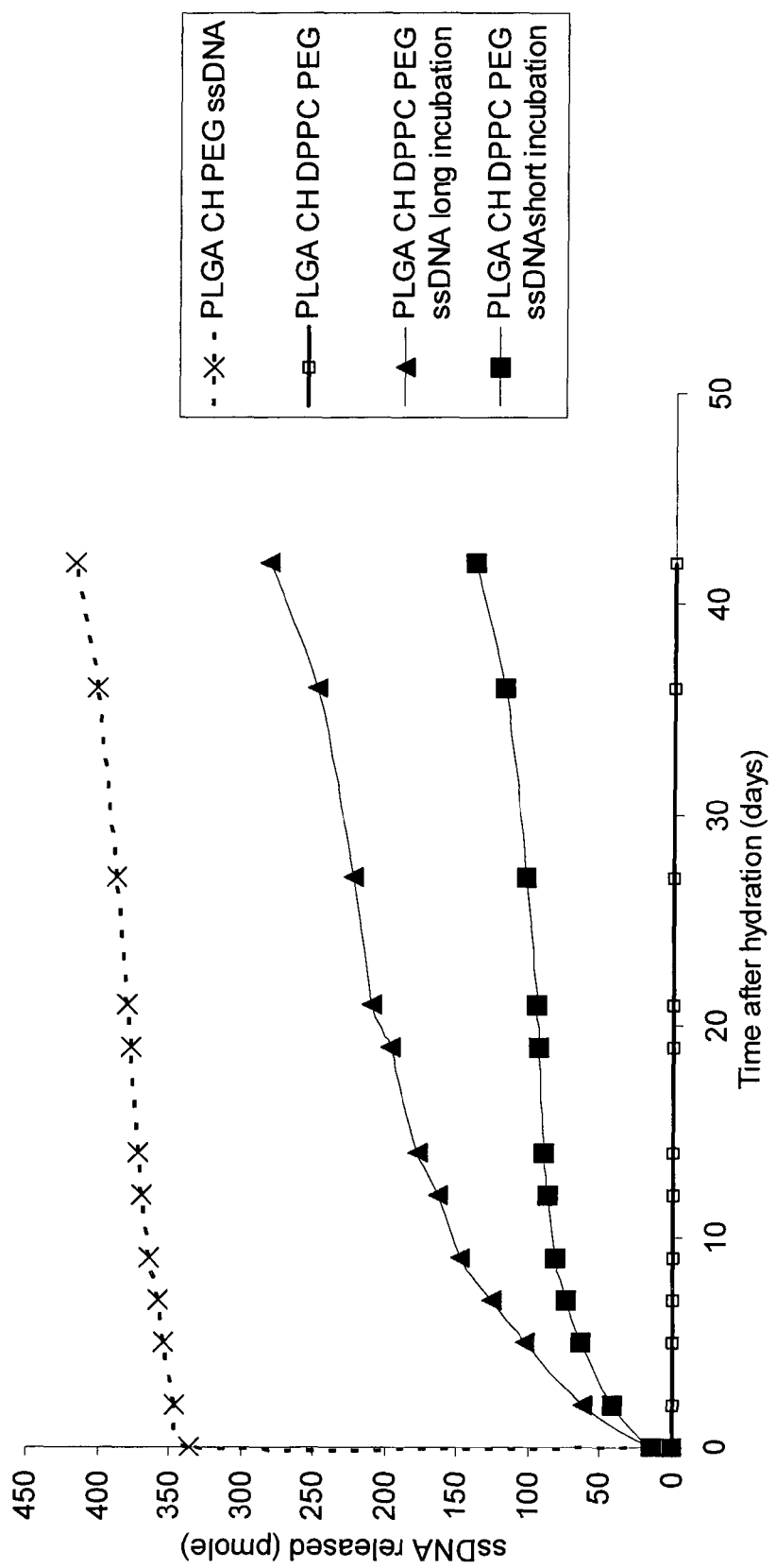
FIG. 6 demonstrates the release rate over time (days) of ssDNA loaded into a matrix composition prepared with polyethylene glycol (PEG) at different incubation times of the ssDNA and PEG.

FIG. 6 shows the accumulated amount of the released ssDNA over time. From this figure, it is clearly demonstrated that (i) the presence of both the polymer and the lipid component are necessary in order to obtain graduate slow release of the ssDNA from the matrix: in the absence of the lipid (DPPC in the particular example) most of the ssDNA is immediately released into the hydration water; and (ii) longer incubation time of the oligonucleotide with PEG results in longer release period of the nucleic acids once the matrix is hydrated.

Example 7

The Influence of the Phospholipids Composition on the Release Rate of ssDNA

Figure 7:
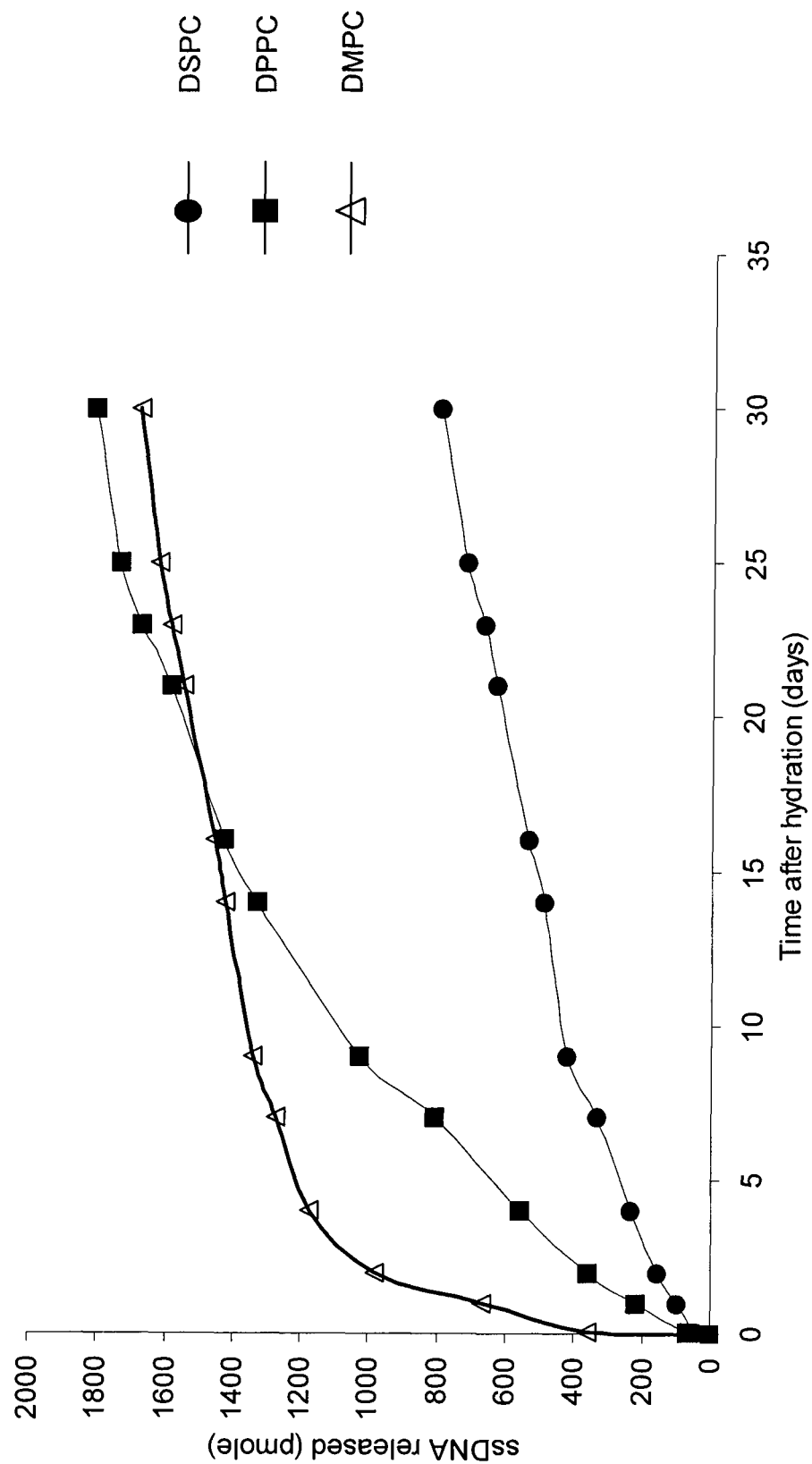
FIG. 7 demonstrates the effect of using phospholipids with different length of fatty acid chains as the main lipid within the matrix composition on the release rate of the loaded ssDNA.

The influence of the phospholipids type and particularly of the length of the phospholipid acyl chains on the rate of ssDNA release from the matrix of the present invention was also examined. FIG. 7 demonstrates that the longer the acyl chains, the lower is the rate of ssDNA release, with DMPC (14:0)>DPPC (16:0)>DSPC (18:0). In the case of DMPC most of the ssDNA is released within the first five days. In contrast a matrix prepared with DPPC released the ssDNA in steady rate (zero order) up to 30 days. In the case of DSPC the rate of release is significantly lower than the other two phospholipids.

Thus, the release rate of ssDNA from the matrix of the invention can be controlled by the phospholipids composition.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A matrix composition comprising:
   a. a biocompatible polymer in non-covalent association with a first lipid component comprising a sterol, wherein the moles of sterol constitute up to 40% of the moles of total lipids present;
   b. a second lipid component comprising at least one phospholipid having fatty acid moieties of at least 14 carbons;
   c. at least one nucleic acid based agent;
   d. a linear polyethylene glycol (PEG) having a molecular weight in the range of 1,000-10,000; and
   e. at least one cationic lipid;
   wherein the matrix composition is substantially free of water, and is adapted for providing sustained and/or controlled release of the nucleic acid ingredient, wherein at least 30% of said agent is released from the composition at zero-order kinetics.

2. The matrix composition of claim 1, wherein the sterol is cholesterol.

3. The matrix composition of claim 2, wherein the cholesterol is present in an amount of 5-50 mole percent of the total lipid content of said matrix composition.

4. The matrix composition of claim 1, wherein the phospholipid in the second lipid component is selected from the group consisting of phosphatidylcholine or a derivative thereof; a mixture of phosphatidylcholines or derivatives thereof; a phosphatidylethanolamine or a derivative thereof; and any combination thereof.

5. The matrix composition of claim 1, wherein said cationic lipid is selected from the group consisting of DC-Cholesterol, 1,2-dioleoyl-3-trimethylammonium-propane (DOTAP), Dimethyldioctadecylammonium (DDAB), 1,2-dilauroyl-sn-glycero-3-ethylphosphocholine (Ethyl PC), 1,2-di-O-octadecenyl-3-trimethylammonium propane (DOTMA) and any combination thereof.

6. The matrix composition of claim 1, wherein the biocompatible polymer is selected from the group consisting of a biodegradable polymer, a non-biodegradable polymer and any combination thereof.

7. The matrix composition of claim 6, wherein the biodegradable polymer is a biodegradable polyester selected from the group consisting of PLA (polylactic acid), PGA (poly glycolic acid), PLGA (Poly (lactic co glycolic acid) and combinations thereof.

8. The matrix composition of claim 6, wherein the non-biodegradable polymer is selected from the group consisting of PEG acrylate, PEG methacrylate, methylmethacrylate, ethylmethacrylate, butylmethacrylate, 2-ethylhexylmethacrylate, laurylmethacrylate, hydroxylethyl methacrylate, 2-methacryloyloxyethylphosphorylcholine (MPC), polystyrene, derivatized polystyrene, polylysine, poly N-ethyl-4-vinyl-pyridinium bromide, poly -methylacrylate, silicone, polyoxymethylene, polyurethane, polyamides, polypropylene, polyvinyl chloride, polymethacrylic acid and combination thereof.

9. The matrix composition of claim 6, wherein the biocompatible polymer comprises a co-block copolymer of a biodegradable polymer and a non-biodegradable polymer.

10. The matrix composition of claim 1, wherein the weight ratio of total lipids to the biodegradable polymer is between 1:1 and 9:1 inclusive.

11. The matrix composition of claim 1, wherein said matrix composition is homogeneous.

12. The matrix composition of claim 1, further comprising at least one compound selected from the group consisting of sphingolipid, tocopherol, a free fatty acid having 14 or more carbon atoms, a PEGylated lipid and an additional phospholipid selected from the group consisting of a phosphatidylserine, a phosphatidylglycerol, and a phosphatidylinositol.

13. The matrix composition of claim 1 wherein the nucleic acid based agent is selected from the group consisting of: plasmid DNA, linear DNA selected from poly and oligonucleotides, chromosomal DNA, messenger RNA (mRNA), antisense DNA/RNA, RNAi, siRNA, microRNA (miRNA), ribosomal RNA, oligonucleotide DNA (ODN) single and double strand, siRNA, CpG imunostimulating sequence (ISS), locked nucleic acid (LNA) and ribozyme.

14. The matrix composition of claim 1, wherein said biocompatible polymer is a biodegradable polyester; and said phospholipid is a combination of a phosphatidylethanolamine having fatty acid moieties of at least 14 carbons and a phosphatidylcholine having fatty acid moieties of at least 14 carbons.

15. An implant comprising the matrix composition of claim 1.

16. A pharmaceutical composition for administering a nucleic based agent to a subject in need thereof, comprising the matrix composition of claim 1.

17. A method of administering a nucleic acid based agent to a subject in need thereof, said method comprising the step of administering to said subject a matrix composition according to claim 1, thereby administering a nucleic acid based agent to a subject in need thereof.

18. A medical device, comprising: a substrate and a biocompatible coating deposited on at least a fraction of said substrate, wherein said biocompatible coating comprises the matrix composition of claim 1.

19. The medical device of claim 18, wherein said biocompatible coating includes multi-layers.

20. A method of producing the matrix composition of claim 1 comprising the steps of:
   a. mixing into a first volatile organic solvent (i) a biocompatible polymer and (ii) a first lipid component comprising at least one lipid having a polar group;
   b. mixing polyethylene glycol into a water-based solution of the nucleic acid agent;
   c. mixing the solution obtained in step (b) with a second volatile organic solvent and a second lipid component comprising at least one phospholipid having fatty acid moieties of at least 14 carbons;
   d. mixing the solutions obtained in steps (a) and (c) to form a homogeneous mixture; and
   e. removing the volatile solvents and water,
   thereby producing a homogeneous polymer-phospholipids matrix comprising the nucleic acid agent, wherein the matrix composition is substantially free of water, and is adapted for providing sustained and/or controlled release of said nucleic acid agent.

21. The method of claim 20, wherein step (c) further comprises (i) removing the solvents by evaporation, freeze drying or centrifugation to form a sediment; and (ii) suspending the resulted sediment in the second volatile organic solvent.

22. The method of claim 20 wherein following step (d) the resulted solution is injected into liquid nitrogen, to water or hot air (spray drier) in order to produce vesicles or is inserted into a mold, and subsequently the liquids are removed in order to get a specific structured matrix.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic peptide (primer)

<400> SEQUENCE: 1
ccatcaacga ccccttcatg gac                                    23

<210> SEQ ID NO 2
<211> LENGTH: 23
<212> TYPE: DNA
<213> ORGANISM: Artificial Sequence
<220> FEATURE:
<223> OTHER INFORMATION: Synthetic peptide (primer)

<400> SEQUENCE: 2
ggatgacctt gcccacagcc ttg                                    23